US006203977B1

(12) United States Patent
Ward et al.

(10) Patent No.: US 6,203,977 B1
(45) Date of Patent: Mar. 20, 2001

(54) DELINEATION OF INDIVIDUAL HUMAN CHROMOSOMES IN METAPHASE AND INTERPHASE CELLS BY IN SITU SUPPRESSION HYBRIDIZATION

(75) Inventors: David C. Ward, Guilford, CT (US); Peter Lichter; Thomas Cremer, both of Heidelberg (DE); Laura Manuelidis, New Haven, CT (US); Thomas Ried, Heidelberg (DE); Antonio Baldini, London (GB)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 08/312,429

(22) Filed: Sep. 26, 1994

Related U.S. Application Data

(63) Continuation of application No. 07/837,664, filed on Feb. 14, 1992, now abandoned, which is a continuation-in-part of application No. 07/271,609, filed on Nov. 15, 1988, now abandoned.

(51) Int. Cl.[7] .............................. C12Q 1/68; C07H 21/04
(52) U.S. Cl. ........................... 435/6; 536/24.3; 536/27.1; 935/77; 935/78
(58) Field of Search .............................. 435/6; 536/24.3, 536/27.1; 935/77, 78

(56) References Cited

U.S. PATENT DOCUMENTS

| | | | |
|---|---|---|---|
| 4,358,535 | * 11/1982 | Falkow et al. ........................... | 435/5 |
| 4,647,529 | * 3/1987 | Rodland et al. ......................... | 435/6 |
| 4,681,840 | * 7/1987 | Stephenson et al. ..................... | 435/6 |
| 4,683,195 | * 7/1987 | Mullis et al. ............................ | 435/6 |
| 4,707,440 | * 11/1987 | Stavrianopoulos ....................... | 435/6 |
| 4,710,465 | * 12/1987 | Weissman et al. ...................... | 435/91 |
| 4,711,955 | * 12/1987 | Ward et al. ............................. | 536/29 |
| 4,721,669 | * 1/1988 | Barton ..................................... | 435/6 |
| 4,725,536 | * 2/1988 | Fritsch et al. ............................ | 435/6 |
| 4,737,454 | * 4/1988 | DaMagupta et al. .................... | 435/6 |
| 4,755,458 | * 7/1988 | Rabbani et al. .......................... | 435/5 |
| 4,770,992 | * 9/1988 | Van den Engh et al. ................ | 435/6 |
| 4,772,691 | * 9/1988 | Herman ................................... | 536/27 |
| 4,888,278 | * 12/1989 | Singer et al. ............................ | 435/6 |
| 5,447,841 | * 9/1995 | Gray et al. .............................. | 435/6 |

FOREIGN PATENT DOCUMENTS

| | | |
|---|---|---|
| 0357436 | 3/1990 | (EP) . |
| 0357437 | 3/1990 | (EP) . |
| 2215724 | 9/1979 | (GB) . |
| 2 019 408 | * 10/1979 | (GB) . |
| 1203108 | * 1/1985 | (SU) ...................................... 935/78 |
| WO87/05027 | 8/1987 | (WO) . |
| WO88/01300 | 2/1988 | (WO) . |

OTHER PUBLICATIONS

Lawrence Livermore National Laboratory, "Chromosome–Specific Human Gene Libraries," *Energy and Technology Review*, 82–83 (1985).

Lawrence Livermore National Laboratory, "Fluorescent Labeling of Human Chromosomes with Recombinant DNA Probes," *Energy and Technology Review* (UCRL 5200–85–7), 84–85 (1985).

LeGrys, V., et al., "Clinical Applications of DNA Probes in the Diagnosis of Genetic Diseases," *CRC Critical Reviews in Clinical Laboratory Sciences*, 25(4):255–274 (1987).

Lewin, B. (editor), Eukaryotic Genomes: A Continum of Sequences (Chapter 18), *Genes* (2nd Edition John Wiley & Sons, Inc.), 293–298 and 464–465 (1984).

Lewin, R., "Genetic Probes Become Ever Sharper" *Science*, 221(4616):1167 (1983).

Lichter, P., et al., "High–Resolution Mapping of Human Chromosome 11 by in Situ Hybridization with Cosmid Clones," *Science*, 247:64–69 (1990).

Lichter, P., et al., "Is Non–isotopic in Situ Hybridization Finally Coming of Age?," *Nature*, 345:93–94 (1990).

Lichter, P., et al., "Rapid Detection of Human Chromosome 21 Aberrations by in Situ Hybridization," *PNAS USA*, 85:9664–9668 (1988).

Litt, M. and White, R.L., "A Highly Polymorphic Locus in Human DNA Revealed by Cosmid–Derived Probes," *PNAS USA*, 82:6206–6210 (1985).

Manuelidis, L. and Ward, D., "Chromosomal and Nuclear Distribution of the Hindlll 1.9–kb Human DNA Repeat Segment," *Chromosoma* (Berl.), 91:28–38 (1984).

Manuelidis, L., "Individual Interphase Chromosome Domains Revealed by in Situ Hybridization" *Hum. Genet.*, 71:288–293 (1985).

Manuelidis, L., "Different Central Nervous System Cell Types Display Distinct and Nonrandom Arrangements of Satellite DNA Sequences" *PNAS USA*, 81:3123–3127 (1984).

McCormick, F., "The Polymerase Chain Reaction and Cancer Diagnosis," *Cancer Cells*, 1(2), 56–61 (1989).

Montgomery, K., et al., "Specific DNA Sequence Amplification in Human Neuroblastoma Cells," *PNAS USA*, 80:5724–5728 (1983).

Nederlof, P., et al., "Detection of Chromosome Aberrations in Interphase Tumor Nuclei by Nonradioactive In Situ Hybridization," *Cancer Genet Cytogenet*, 42:87–98 (1989).

Olsen, A., et al., "Isolation of Unique Sequence Human X Chromosomal Deoxyribonucleic Acid," *Biochemistry*, 19:2419–2428 (1980).

(List continued on next page.)

Primary Examiner—Jasemine C. Chambers
Assistant Examiner—Scott D. Priebe
(74) *Attorney, Agent, or Firm*—Lahive & Cockfield, LLP; Giulio A. DeConti, Jr., Esq.

(57) ABSTRACT

This disclosure relates to a method of specifically decorating selected mammalian chromosomes and of detecting, identifying and and/or quantitating selected individual chromosomes, by means of chromosomal in situ suppression (CISS) hybridization. The method is useful in analyzing cells for the occurrence of chromosomes, chromosome fragments or chromosome aberrations.

32 Claims, 16 Drawing Sheets

OTHER PUBLICATIONS

Pinkel, D., et al., "Cytogenetic Analysis by in Situ Hybridization With Fluorescently Labeled Nucleic Acid Probes," *Cold Spring Harbor Symposia on Quantitative Biology*, L1:151–157 (1986).

Pinkel, D., et al., "Cytogenetic Analysis During Leukemia Therapy Using Fluorescence in Situ Hybridization with Chromosome–Specific Nucleic Acid Probes," *Am. J. Hum. Genet.* (Supplement), 41(3), A34 (096; 12.12) (1987).

Pinkel, D. et al., "Cytogenetics Using Fluorescent Nucleic Acid Probes and Quantitative Microscopic Measurement," (UCRL 93269 Abstract), *Analytical Cytology X Conference*, Hilton Head Resort, SC, (Nov. 17–22, 1985).

Fuscoe, J., et al., "An Efficient Method for Selecting Unique–Sequence Clones from DNA Libraries and Its Application to Fluorescent Staining of Human Chromosome 21 Using in Situ Hybridization," *Genomics*, 5:100–109 (1989).

Gall, J. and Pardue, M., "Formation and Detection of RNA–DNA Hybrid Molecules in Cytological Preparations," *PNAS USA* , 63:378–383 (1969).

Gray, J.W., et al., "Fluorescence Hybridization to Human Chromosome 21 Using Probes from a Charon 21 A Library," *Cytometry*, (Suppl. 1), Abst. 19, p. 4 (1987).

Gray, J.W., et al., "Quantitative Cytogenetics: Progress Report on the Development of Fuorescence Hybridization for Specific Chromosome Staining," (Abstract) Lawrence Livermore National Laboratory, Livermore, CA (UCRL 93567).

Grunstein, M., et al., "Colony Hybridization: A Method for the Isolation of Cloned DNAs That Contain a Specific Gene," *PNAS, USA* 72(10):3961–3965 (1975).

Harper, M. and Saunders, G., "Localization of Single Copy DNA Sequences on G–Banded Human Chromosomes by in Situ Hybridization," *Chromosoma (Berl.)*, 83:431–439 (1981).

Harper, M., et al., "Localization of the Human Insulin Gene to the Distal end of the Short Arm of Chromosome 11," *PNAS USA*, 78(7):4458–4460 (1981).

Herzenberg, L., et al., "Fetal Cells in the Blood of Pregnant Women: Detection and Enrichment by Fluorescence–Activated Cell Sorting," *PNAS USA*, 76(3):1453–1455 (1979).

Hood, L., et al., *Molecular Biology of Eucaryotic Cells*, W.A. Benjamin, Inc. Menlo Park, Calif., CH. 2–10, 47–51 (1975).

Jabs, E., et al., "Characterization of a Cloned DNA Sequence That is Present at Centromeres of all Human Autosomes and the X Chromosome and Shows Polymorphic Variation," *PNAS USA*, 81:4884–4888 (1984).

John, H.A., et al., "RNA–DNA Hybrids at the Cytological Level," *Nature*, 223:582–587 (1969).

Kao, F., et al., "Assignment of the Structural Gene Coding for Albumin to Human Chromosome 4," *Human Genetics*, 62:337–341 (1982).

Kievits, T., et al., "Direct Nonradioactive in Situ Hybridization of Somatic Cell Hybrid DNA to Human Lymphocyte Chromosomes," *Cytometry*, 11:105–109 (1990).

Landegent, J.E., et al., "2–Acetylaminofluorene–modified Probes for the Indirect Hybridocytochemical Detection of Specific Nucleic Acid Sequences", *Experimental Cell Research*, 153:61–72 (1984).

Landegent, J.E., et al., "Chromosomal Localization of a Unique Gene by Non–Autoradiographic in Situ Hybridization," *Nature*, 317:175–177 (1985).

Langer–Safer, P., et al., "Immunological Method for Mapping Genes on Drosophila Polytene Chromosomes," *PNAS USA*, 79:4381–4385 (1982).

Lawrence, J., et al., "Sensitive, High–Resolution Chromatin and Chromosome Mapping In Situ: Presence and Orientation of Two Closely Integrated Copies of EBV in a Lymphoma Line," *Cell*, 52:51–61 (1988).

Pinkel, D., et al., "Detection of Structural and Numerical Abnormalities in Metaphase Spreads and Interphase Nuclei in Situ Hybridization," *Cancer Genet and Cytogenet* (UCRL 101043 Abstract 34), 41:236 (1989).

Pinkel, D., et al., "Fluorescence in Situ–Hybridization with Human Chromosome–Specific Libraries: Detection of Trisomy 21 and Translocations of Chromosome 4," *PNAS USA*, 85:9138–9142 (1988).

Pinkel, D., et al., "Genetic Analysis by Quantitative Microscopy and Flow Cytometry Using Fluorescence in Situ Hybridization with Chromosome–Specific Nucleic Acid Probes," *Am. J. Hum. Genet.* (Supplement),vol.39:3, A129 (379) (Sep. 1986).

Pinkel, D., et al., "Rapid, Quantitative Cytogenetic Analysis Using Fluorescently Labeled Nucleic Acid Probes," (UCRL 93553 Abstract), U.S.–Japan Joint Environmental Panel Conf., Research Triangle Park, NC, (Oct. 21–23, 1985).

Pinkel, D., et al., "Simplified Cytogenetics Using Biotin Labeled Nucleic Acid Probes and Quantitative Fluorescence Microscopy," (UCRL 93243 Abstract), *American Journal of Human Genetics* (Supplement), 37(4):A112 (Jul. 1985).

Rappoid, G.A., et al., "Sex Chromosome Positions in Human Interphase Nuclei as Studied by in Situ Hybridization with Chromosome Specific DNA Probes," *Human Genetics*, 67:317–325 (1984).

Roelofs, H., et al., "Gene Amplification in Human Cells May Involve Interchromosomal Transposition and Persistence of the Original DNA Region", *The New Biologist*, 4(1):75–86 (1992).

Scalenghe, F., et al., "Microdissection and Cloning of DNA from a Specific Region of *Drosophila melanogaster* Polytene Chromosomes," *Chromosoma (Berl.)*, 82:205–216 (1981).

Schardin, M., et al., "Specific Staining of Human Chromosomes in Chinese Hamster X man Hybrid Cell Lines Demonstrates Interphase Chromosome Territories," *Hum Genet*, 71:281–287 (1985).

Schmeckpeper, b., et al., "Partial purification and characterization of DNA from the human X chromosome," *PNAS USA*, 76(12):6525–6528 ( 1979).

Sealy et al., "Removal of repeated sequences from hybridisation probes," *Nucleic Acids Research*, 13(6):1905–1922 (1985).

Selypes et al., "A Noninvasive Method for Determination of the Sex and Karyotype of the Fetus From the Maternal Blood," *Hum. Genet.*, 79:357–359 (1988).

Smith et al., "Distinctive Chromosomal Structures Are Formed Very Early in the Amplification of CAD Genes in Syrian Hamster Cells," *Cell*, 63:1219–1227 (1990).

Sparkes et al., "Regional Assignment of Genes for Human Esterase D and Retinoblastoma in Chromosome Band 13q14," *Science*, 208:1042–1044 (1988).

Stewart et al., "Cloned DNA probes regionally mapped to human chromosome 21 and their use in determining the original of nondisjunction," *Nucleic Acids Research*, 13(11);4125–4132 (1985).

Straume et al., "Chromosome translocations at low radiation doses quantified using fluorescent DNA probes," Radiation Research Society Meeting (UCRL 93837 (Abstract), Las Vegas, NV (Apr. 12–17, 1986).

Szabo and Ward, "Emerging Techniques. What's new with hybridization in situ?" *TIBS*, 7(11):425–427 (1982).

Trask et al., "Detection of DNA sequences in nuclei in suspension by in situ hybridization and dual beam flow cytometry," Analytical Cytology X Conference (UCRL 93372 Abstract), Hilton Head Resort, SC (Nov. 17–22, 1985).

Trask et al., "The Proximity of DNA Sequences in Interphase Cell Nuclei is Correlated to Genomic Distance and Permits Ordering of Cosmids Spanning 250 Kilobase Paris," *Genomics*, 5:710–717 (1989).

Trask et al., "Early dihydrofolate reductase gene amplification events in CHO cells usually occur on the same chromosome arm as the original locus," *Genes & Development*, 3:1913–1925 (1989).

Trent et al., "Report of the committee on structural chromosome changes in neoplasia," *Cytogenet Cell Genet*, 51:533–562 (1989).

Van Dilla and Deaven (Abstract), "Construction and Availability of Human Chromosome–Specific DNA Libraries from Flow Sorted Chromosomes: Status Report," *Am J. of Human Genetics*, 37, (R. Supplement) (Jul. 1985).

Wallace et al., "The use of synthetic oligonucleotides as hybridization probes. II. Hybridization of oligonucleotides of mixed sequence to rabbit β–globin DNA," *Nucleic Acids Research*, 9(4):879–894 (1981).

Weiss et al., "Organization and evolution of the class I gene family in the major histocompatibility complex of the C57BL/10 mouse," *Nature*, 310:650–655 (1984).

Willard et al., "Isolation and characterization of a major tandem repeat family from the human X chromosome," *Nucleic Acids Research*, 11(7):2017–2033 (1983).

Windle et al., "A central role for chromosome breakage in gene amplification, deletion formation, and amplicon integration" *Genes & Development*, 5:160–174 (1991).

Yunis et al., "Localization of Sequences Specifying Messenger RNA to Light–Staining G–Bands of Human Chromosomes" *Chromosoma* (Berl.), 61:335–344 (1977).

Litt et al., *Proc. Natl. Acad. Sci. USA* 82:6206–6210 (1985).

Albertson, D., "Localization of the Ribosomal Genes in *Caenorhabditis Elegans* Chrom0somes by in Situ Hybridization Using Biotin–Labeled Probes," *EMBO Journal*, 3(6)1227–1234 (1984).

Albertson, D., "Mapping Muscle Protein Genes by in Situ Hybridization Using Biotin–Labeled Probes," *EMBO Journal*, 4(10):2493–2498 (1985).

Ardeshir, F., et al., "Structure of Amplified DNA in Different Syrian Hamster Cell Lines Resistant to N–(Phosphonacetyl)–L–Aspartate," *Molecular and Cellular Biology*, 3(11):2076–2088 (1983).

Arnoldus, E.P.J., et al., "Detection of the Philadelphia Chromosome in Interphase Nuclei (With 2 Color Plates)," *Cytogenet Cell Genet.*, 54:108–111 (1990).

Bar–Am, I., et al., "Detection of Amplified DNA Sequences in Human Tumor Cell Lines by Fluorescence in Situ Hybridization," *Genes, Chromosomes & Cancer*, 4:314–320 (1992).

Benton, W. and Davis, R., "Screening λgt Recombinant Clones by Hybridization to Single Plaques in situ," *Science*, 196:180–182 (1977).

Bergerheim, U., et al., "Deletion Mapping in Human Renal Cell Carcinoma[1]," *Cancer Research*, 49:1390–1396 (1989).

Bookstein, R., et al., "Human Retinoblastoma Susceptibility Gene: Genomic Organization and Analysis of Heterozygous Intragenic Deletion Mutants," *PNAS (USA)*, 85:2210–2214 (1988).

Brison, O., et al., "General Method for Cloning Amplified DNA by Differential Screening with Genomic Probes," *Molecular and Cellular Biology*, 2(15):578–587 (1982).

Britten, R., et al., "Analysis of Repeating DNA Sequences by Reassociation" *Methods of Enzymology*, 29:363–418 (1974).

Buonigiorno–Nardelli, M., "Autoradiographic Detection of Molecular Hybrids between rRNA and DNA in Tissue Sections," *Nature*, 225:946–948 (1970).

Cannizzaro, L.A., et al., "In Situ Hybridization and Translocation Breakpoint Mapping," *Cytogenet Cell Genet*, 39:173–178 (1985).

Cohen, A., et al., "Hereditary Renal–Cell Carcinoma Associated with a Chromosomal Translocation," *The New England Journal of Medicine*, 301(11):592–595 (1979).

Collins, F. and Weissman, S., "Directional Cloning of DNA Fragments at a Large Distance from an Initial Probe: A Circularization Method," *PNAS (USA)*, 81:6812–6816 (1984).

Cox, K., et al., "Detection of mRNAs in Sea Urchin Embryos by in Situ Hybridization Using Asymmetric RNA Probes," *Developmental Biology*, 101:485–502 (1984).

Cremer, T., et al., "Detection of Chromosome Aberrations in the Human Interphase Nucleus by Visualization of Specific Target DNAs with Radioactive and Non–Radioactive in Situ Hybridization Techniques: Diagnosis of Trisomy 18 with Probe L1.84," *Hum. Genet.*, 74:346–352 (1986).

Cremer, T., et al., "Rapid Metaphase and Interphase Detection of Radiation–Induced Chromosome Aberrations in Human Lymphocytes by Chromosomal Suppression In Situ Hybridization," *Cytometry*, 11:110–118 (1990).

Durnam, D., et al., "Detection of Species Specific Chromosomes in Somatic Cell Hybrids," *Som. Cell Molec. Genetics*, 11(6):571–577 (1985).

Erikson, J., et al., "Heterogeneity of Chromosome 22 Breakpoint in Philadelphia–Positive(Ph+) Acute Lymphocytic leukemia," PNAS USA, 83:1807–1811 (1986).

Fisher, J.H., et al., "Molecular Hybridization Under Conditions of High Stringency Permits Cloned DNA Segments Containing Reiterated DNA Sequences to be Assigned to Specific Chromosomal Locations," *PNAS USA*, 81:520–524 (1984).

Friend, S., et al., "A Human DNA Segment with Properties of the Gene that Predisposes to Retinoblastoma and Osteosarcoma," *Nature*, 323:643–646 (1986).

Ried et al., "Multicolor in situ hybridization with PCR labeled probes and digital imaging "Am. J. Human Genet. 49 (4 suppl.): Oct. 19, 1991.*

Nederlof et al., "Multiple fluorescence in situ hybridization", Cytometry 11: 126–131, 1990.*

Pinkel et al. (1986) "Cytogenetic analysis using quantitative, high–sensitivity fluorescene hybridization"Proc. Natl. Acad. Sci. USA 83: 2934–38.*

Lichter et al. (1988) "Dilmeation of individual human chromosomes in Metaphase and interphase cells by in situ suppression hybridization etc.", Hum. Gen. 80:224–234.*

Cremer et al. (1988) "Detection of chromones aberrations in metaphase and interphase tumor cells by in situ hybridization using chromones specific probes,"Hum. Gen. 80:235–246.*

Hanes et al., Nucleic Acid Hybridization, CRL Press, Oxford, Hopman et al., Histochemistry (1986) 85:1–4.*

Devilee et al., Cancer Research, v. 48, Oct. 15, 1988, 5825–30.*

Viegas–Pequiqnet et al., Proc. Natl. Acad. Sci. USA, v. 86, 1989, pp. 582–6.*

Pinkel et al., Amer. J. Human Genetics, Sep. 1, 1988, vol. 43, p.118.*

Landegent et al., Human Genet (1987) 77:366–370.*

Gray et al., Abstract for XII Intl Ltg Soc. Analytical Cytology, Aug. 1987.*

Cremer et al., Experimental Cell Res, 176(1988) 199–220.*

* cited by examiner

FIG.3A
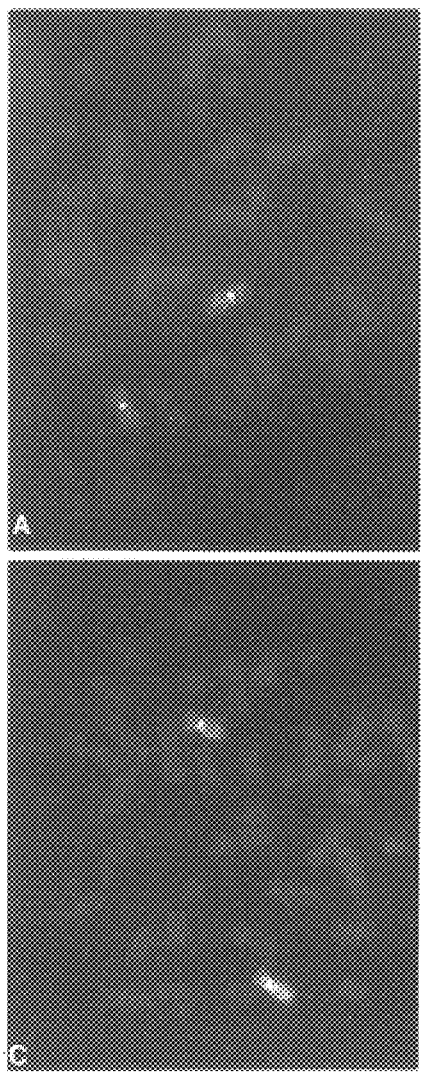
FIG.3B
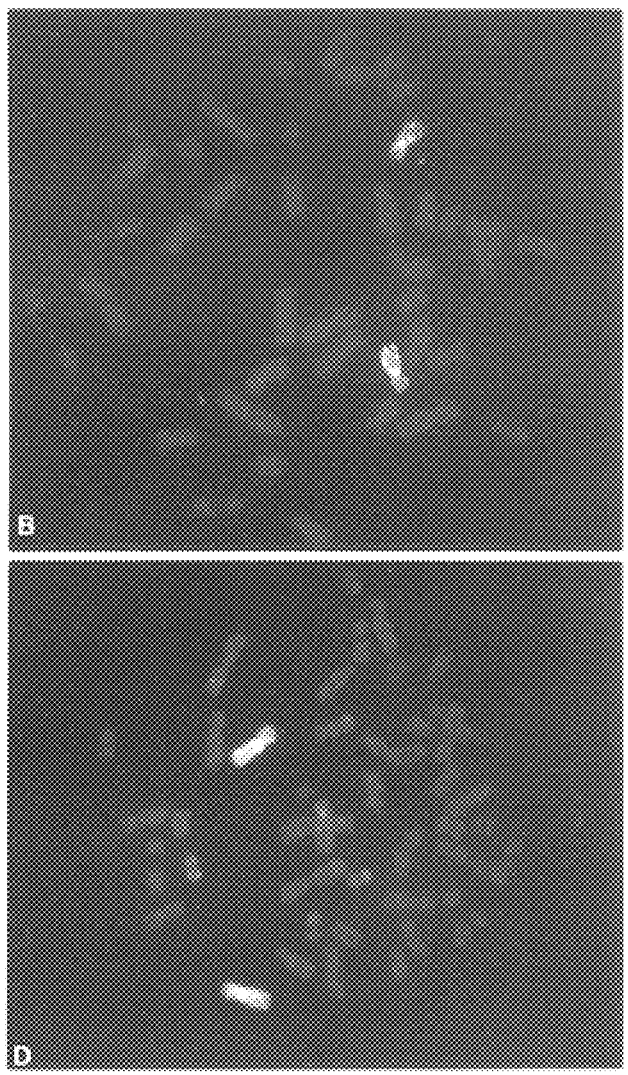
FIG.3C
FIG.3D

FIG.6A     FIG.6B
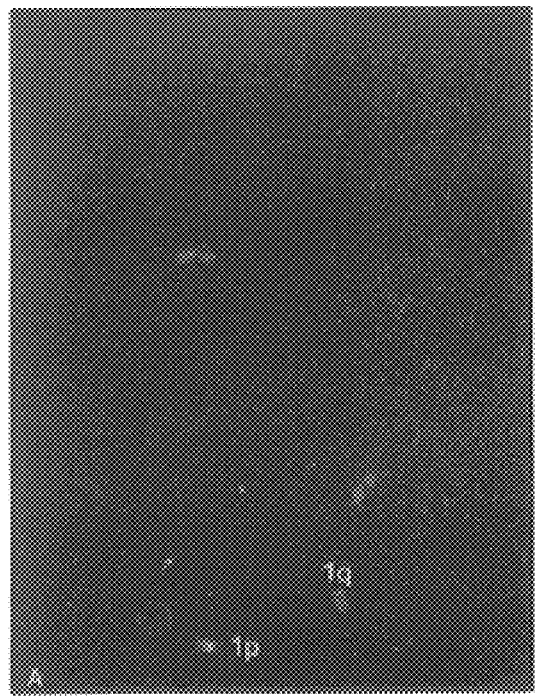
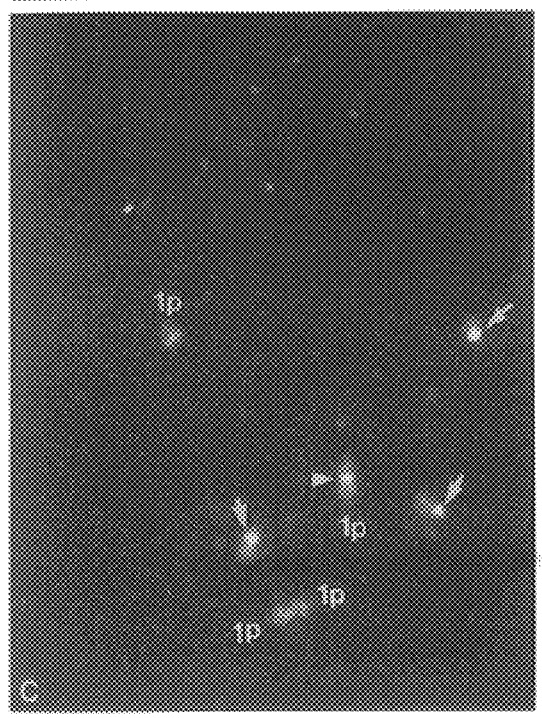
FIG.6C     FIG.6D

FIG.7A FIG.7B FIG.7C FIG.7D
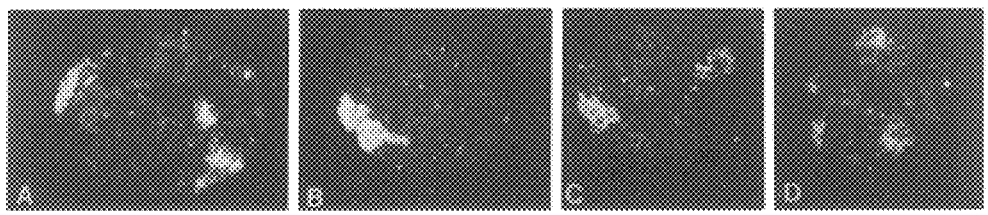
FIG.7E FIG.7F
 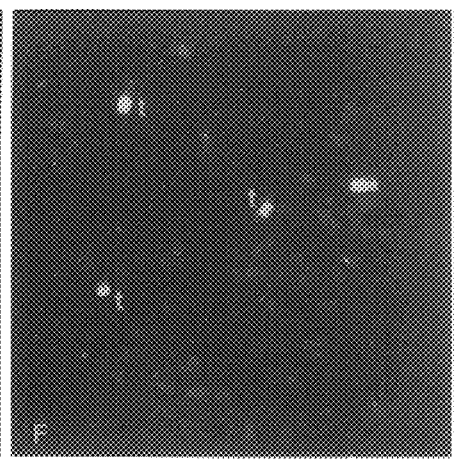
FIG.7G FIG.7H
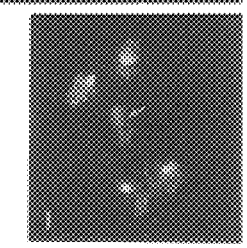
FIG.7I
FIG.7J
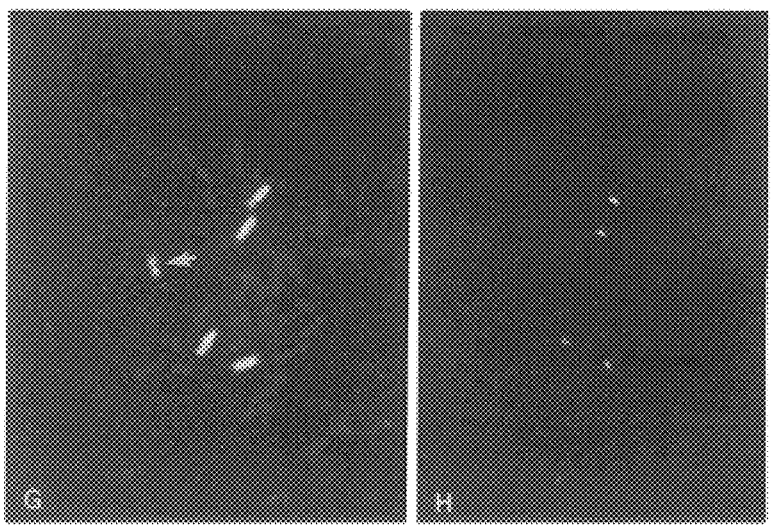
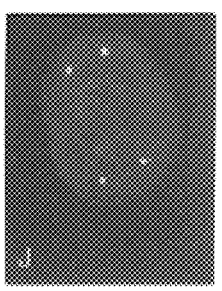

FIG.8A
FIG.8B
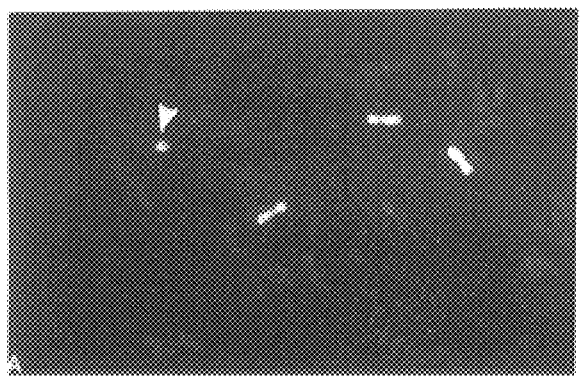
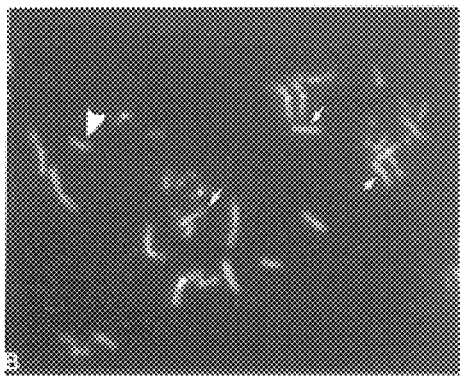
FIG.8C
FIG.8D
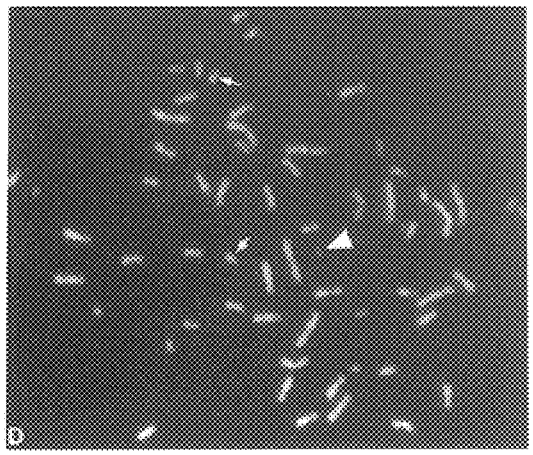
FIG.8E
FIG.8F  FIG.8G
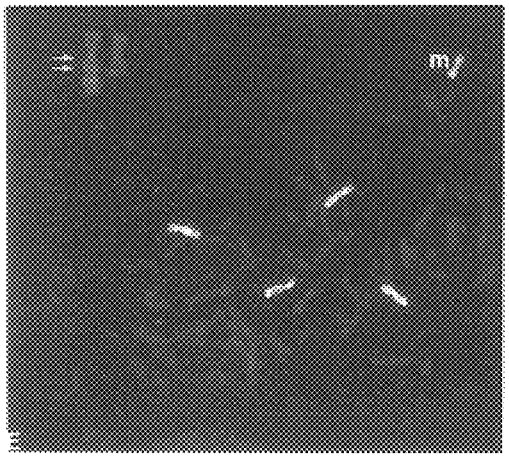
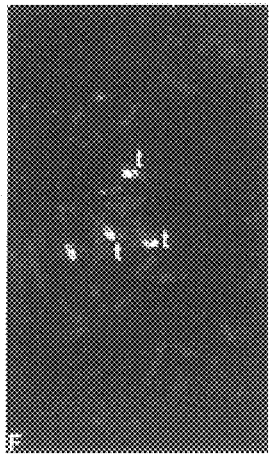
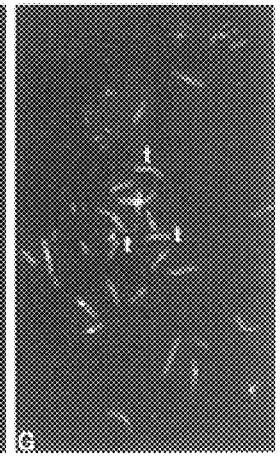

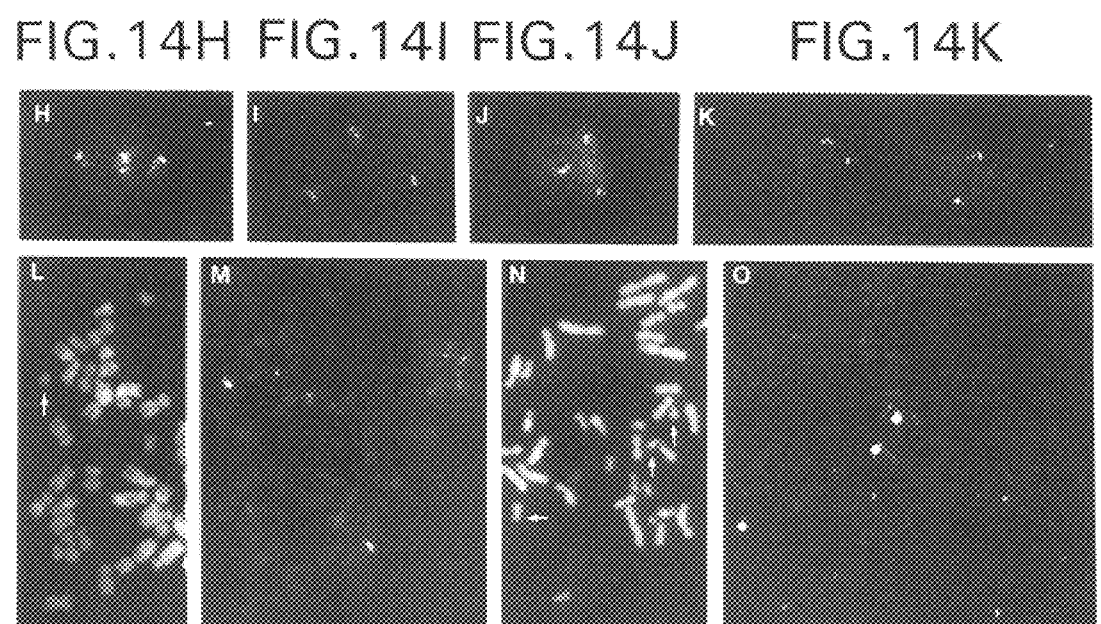

DELINEATION OF INDIVIDUAL HUMAN CHROMOSOMES IN METAPHASE AND INTERPHASE CELLS BY IN SITU SUPPRESSION HYBRIDIZATION

This application is a continuation of application Ser. No. 07/837,664, filed Feb. 14, 1992 which is a continuation-in-part of application Ser. No. 07/271,609 filed Nov. 15, 1988, both abandoned.

FUNDING

Work described herein was supported by Grant numbers GM-32156 and CA-15044 awarded by the National Institutes of Health. The United States Government has certain rights in the invention.

BACKGROUND

Chromosome banding techniques have facilitated the identification of specific human chromosomes and presently provide the major basis upon which chromosomal aberrations are diagnosed. The interpretation of chromosome banding patterns requires skilled personnel and is often technically difficult, especially with respect to detecting minor structural changes and when analyzing complex karyotypes, such as those of highly aneuploid tumor cells. An additional complexity is that readable metaphase chromosome spreads are sometimes very difficult or impossible to prepare from certain cell types or tissues. Alternative methods for identifying chromosomal aberrations would be valuable because they could augment current methods of cytogenic analysis, particularly if such alternative methods were applicable to both mitotic and interphase cell populations.

Over the past few years, a considerable body of evidence has been obtained which indicates that the DNA of individual chromosomes occupy focal territories, or spatially cohesive domains, within mammalian interphase nuclei. Cremer, T. et al., *Hum. Genet.*, 60:46–56 (1982); Hens, L. et al., *Exp. Cell Res.*, 149:257–269 (1983); Schardin, M. et al., *Hum. Genet.*, 71:281–287 (1985); Manuelidis, L., *Hum Genet.*, 71:288–293 (1985); and Pinkel, D. et al., *Proc. Natl. Acad. Sci. USA*, 83:2934–2938 (1986). These observations suggest that chromosome-specific probe sets could be used to detect numerical or structural aberrations of chromosomal domains in non-mitotic cells, an approach termed "interphase cytogenics". Cremer, T. et al., *Hum. Genet.*, 74:346–352 (1986). Indeed, recent in situ hybridization studies have demonstrated the prenatal diagnosis of trisomy-18 with interphase cells and the detection of numerical chromosomal abnormalities in tumor cells lines using chromosome-specific repetitive DNAs as probes. Cremer, T. et al., *Hum. Genet.*, 74:346–352 (1986) and Cremer, T. et al., *Exp. Cell Res.*, 176:119–220 (1988). All chromosome-specific repetitive DNAs reported to date are localized to discrete subregions of each chromosome and, thus, such DNA probes are unsuitable for analyses of many types of chromosomal aberrations (e.g., translocations and deletions). If it were possible to detect uniquely the spectrum of sequences comprising a specific chromosome, analysis of aberrations of chromosomal domains in non-mitotic cells would be possible. Furthermore, such a general labeling technique would make it possible to address fundamental questions concerning the spatial organization of chromosomal DNA within interphase nuclei.

DISCLOSURE OF THE INVENTION

The subject invention relates to a method of detecting, identifying and/or quantitating selected individual chromsomes in mammalian mitotic or interphase cells, by means of chromosomal in situ suppression (CISS) hybridization and its use in analyzing cells for the occurrence of chromosomes, chromosome fragments, or chromosome aberrations, such as those associated with a condition or disease. In the method of the present invention, chromosome-specific probes (DNA or RNA) are combined with a sample to be analyzed, in such a manner that an individual chromosome(s) of interest is labeled and the complex spectrum of sequences which comprise the chromosome can be detected. The probes used in the present method are of high genetic complexity and can be appropriately-selected cloned DNA or RNA fragments, used individually or in pools, or chromosome library DNA.

The method of the present invention, referred to as CISS hybridization, is particularly useful because it can be used to specifically stain individual mammalian chromosomes at any point in the cell cycle. It can be used to assess chromosomal content, particularly chromosome aberrations (e.g., deletions, rearrangements, change in chromosome number) which, until the present invention, it has been time-consuming and/or difficult, if not impossible, to detect. The method is useful in providing a rapid and highly specific assessment of individual mammalian chromosomes in any context (e.g., diagnosis and/or monitoring of a genetic condition or a disease state) in which such an assessment is desired.

BRIEF DESCRIPTION OF THE DRAWINGS

FIG. 2A shows prehybridization with 0 $\mu$g/ml human competitor DNA.

FIG. 2B shows prehybridization with 50 $\mu$g/ml of human competitor DNA.

FIG. 2C shows prehybridization with 100 $\mu$g/ml of human competitor DNA.

FIG. 2D shows prehybridization with 200 $\mu$g/ml of human competitor DNA.

FIG. 2E shows prehybridization with 1000 $\mu$g/ml of human competitor DNA.

FIG. 2F is the same as FIG. 2E except that the metaphase spread is post-stained with DAPI.

FIGS. 3A–3D show the effect of pre-annealing time on the specificity and strength of the hybridization signal. Biotin-labeled chromosome 7 DNA inserts (20 $\mu$g/ml) were preannealed with 200 $\mu$g/ml human competitor DNA for different times prior to hybridization to metaphase chromosomes.

FIG. 3A shows preannealing for 0 minutes.

FIG. 3B shows preannealing for 2 minutes.

FIG. 3C shows preannealing for 5 minutes.

FIG. 3D shows preannealing for 20 minutes.

FIG. 5A and FIG. 5B show domains for chromosome 1. Hybridization to acetic acid-methanol fixed nuclei was detected by fluorescein isothiocyanate (FITC)-conjugated avidin.

FIG. 5C and FIG. 5D show domains for chromosome 7. Hybridization to acetic acid-methanol fixed nuclei was detected by fluorescein isothiocyanate (FITC)-conjugated avidin. A predominant staining of the centromere region is seen within the chromosome 7 domains, reflecting preferential hybridization of the chromosome 7-specific alphoid DNA repeat; a similar signal distribution on metaphase chromosomes was also observed in the particular experiment.

FIG. 5E shows domains for chromosome 18. Hybridization to acetic acid-methanol fixed nuclei was detected by fluorescein isothiocyanate (FITC)-conjugated avidin.

FIG. 5F shows domains for chromosome 18. Hybridization to acetic acid-methanol fixed nuclei was detected by alkaline phosphatase-conjugated avidin.

FIG. 6A shows chromosomal in situ suppression (CISS) hybridization of chromosome 1 inserts to metaphase spreads of the TC 620 glioma cell line detected with FITC-avidin.

FIG. 6B is the same as FIG. 6A except that the metaphase spreads are post-stained with 4,6-diamidino-2-phenylindole dihydrochloride (DAPI). TC 620 show two apparently complete 1 chromosomes (small arrows in B) and two marker translocation chromosomes (arrowheads) specifically decorated by these inserts. One of the two marker chromosomes contains a 1p (lower left), the other a 1q arm (lower right); the 1p terminal (relatively GC rich region) in the two normal chromosomes and submetacentric marker is less completely delineated. Also, the 1q12 regions here show little decoration in contrast to most experiments. X950.

FIG. 6C shows chromosomal in situ suppression (CISS) hybridization of chromosome 1 inserts to metaphase spreads of the TC 593 glioma cell line detected with FITC-avidin.

FIG. 6D is the same as FIG. 6C except that the metaphase spreads are post-stained with 4,6-diamidino-2-phenylindole dihydrochloride (DAPI). Typical TC 593 metaphase spreads show six specifically decorated chromosomes. Three acrocentric marker chromosomes all with truncation of 1p show particularly intense fluorescence of repeats that localize to 1q12 (arrows in C). In two of these, 1q arms appear to be complete, while a major deletion is obvious in the third (arrow in D). A forth decorated chromosome (small arrowhead in C, D) again shows a major deletion of the distal part or 1q, but has retained an apparently complete 1p arm. A fifth submetacentric chromosome (large arrowhead) contains an apparently complete 1p arm; the DNA of its short arm is not identified. Note the similarity of this marker to one of the marker chromosomes of TC 620 (1p) described above. The sixth entirely decorated chromosome is an iso (1p) as demonstrated by DAPI-binding (open arrows). X 1200.

FIGS. 7A–7J show CISS hybridization of chromosome 4 library inserts detected with FITC-avidin.

FIG. 7A shows interphase nuclei of TC 593. Note that the two apparently complete interphase domains are widely separated.

FIG. 7B shows interphase nuclei of TC 593. Note that the two apparently complete interphase domains are close to each other.

FIG. 7C shows interphase nuclei of TC 593. Note that the two apparently complete interphase domains are widely separated.

FIG. 7D shows interphase nuclei of TC 620 showing four chromosome 4 interphase domains of largely different size.

FIG. 7E shows metaphase spread of TC 593 showing two apparently complete 4 chromosomes, and a small decorated region (arrow) in a submetacentric chromosome. This marker with translocated 4 sequences was observed in about 30% of the spreads.

FIG. 7F shows metaphase spread of TC 620 showing one apparently complete chromosome 4 and three translocation markers (t) containing different amounts of chromosome 4 material.

FIG. 7G shows double hybridization of biotinylated chromosome 7 inserts and an aminoacetylfluorene (AAF)-modified 7-specific alphoid repeat. Chromosome 7 inserts depict five entirely decorated metaphase chromosomes. Four of them are complete 7 chromosomes, the fifth (arrow) is an iso (7p) (see FIG. 3E).

FIG. 7H shows the same field as G showing AAF-7 alphoid signals on only four decorated chromosomes; no signal is detected on the iso (7p).

FIG. 7I shows an interphase nucleus of TC 593 showing five domains delineated by chromosome 7 inserts. The arrow represents the iso (7p) marker in interphase.

FIG. 7J shows the same field as I showing that four of the domains are labeled by 7 alphoid probes.

FIG. 8A shows CISS hybridization of library inserts of chromosome 7 to metaphase spreads of TC 620 glioma cells detected with FITC-avidin. x 875. Three apparently normal 7 chromosomes and an additional translocation chromosome containing 7 sequences are indicated by large arrowhead.

FIG. 8B is the same as for FIG. 8A except counter-stained with DAPI. DAPI-stained complete chromosomes are indicated by small arrowheads. Other studies (see the text) indicated a translocation of 7pter-q11 in the marker chromosome (large arrowhead).

FIG. 8C shows CISS hybridization of library inserts of chromosome 18 to metaphase spread of TC 620 glioma cells detected with FITC-avidin. Two apparently complete 18 chromosomes and a truncated minute chromosome (large arrowhead) are shown.

FIG. 8D is the same as for FIG. 8C except counter-stained with DAPI.

FIG. 8E shows metaphase spread from pseudotetraploid TC 593 cells showing five chromosomes highlighted by 7 library inserts. The metacentric chromosome (m) represents the iso (7p) marker typical for this line (see also FIG. 2G). Insert chromosomes (small arrows) show DAPI-stained normal and metacentric 7 chromosomes. The landmark band 7q21 and a block of constitutive heterochromatin at 7q11 are both prominent on the normal chromosome 7 insert (arrows) but not present on the marker chromosome. Instead both arms of the latter show a mirror-like staining pattern with a faint distal band at 7p21.

FIG. 8F shows CISS hybridization of library inserts of chromosome 18 to metaphase spreads of TC 593 glioma cells detected with FITC-avidin. Four decorated 18 chromosomes are shown.

FIG. 8G is the same as for FIG. 8F except counter-stained with DAPI. Three decorated 18 chromosomes are clearly translocated.

FIGS. 1–3).

FIG. 10A: Detection of the 7p translocation (t) in a prophase TC 620 nucleus. X 1,000.

FIG. 10B: Detection of five well-separated chromosome 7 domains in interphase TC 593. X 1.240.

FIG. 10C: Detection of two large and one very small 18 domains (indicated by arrowheads) in interphase TC 6. X 1,450.

FIG. 10D: Detection of four chromosome 18 domains in interphase TC 593; one of these signals (arrows) appears smaller. X 1,450.

FIG. 10E: Detection of four chromosomal 1 domains detected in interphase TC 620 (cl. FIGS. 1A, 1B). X 1,200.

FIG. 10F: Detection of at least five chromosome 1 domains in interphase TC 5()3; one (arrow head) is appreciably smaller than the others. X 1,250.

FIG. 10G: CISS hybridization of a metaphase spread of TC 593 with chromosome 18.

FIG. 10H: The same as for 10G except counter-stained with DAPI. The technically poor metaphase spread still highlights four distinct chromosomes bearing 18 sequencer. X 1,000.

FIG. 11A: Counts of 7 specific alphoid repeats (white columns) compared to 7 library inserts (shaded columns) from interphase nuclei of phytohemagglutinin-stimulated human lymphocytes (46, XY).

FIG. 11B: The same as for FIG. 11A except from TC 620 interphase nuclei (7-specific alphoid repeats) and metaphase spreads (7 library inserts).

FIG. 11C: The same as for FIG. 11A except from TC 593 interphase nuclei (7-specific alphoid repeats) and metaphase spreads (7 library inserts).

Figure 11A:
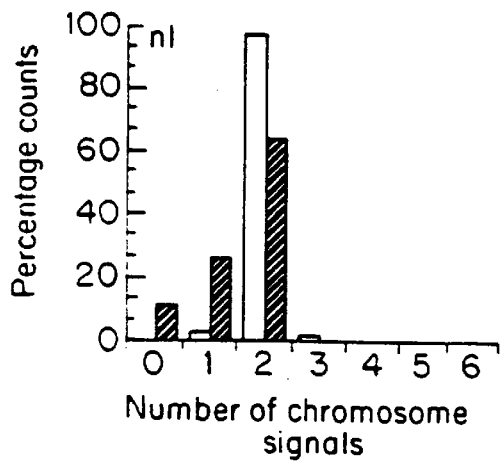
FIGS. 11A–11E are graphic representations of the interphase and/or metaphase counts of chromosomes 7, 22 and 4 by CISS hybridization. Interphase counts were performed on 150 nuclei of well-hybridized preparations. For metaphase counts >25 complete DAPI-stained spreads were evaluated.
Figure 11B:
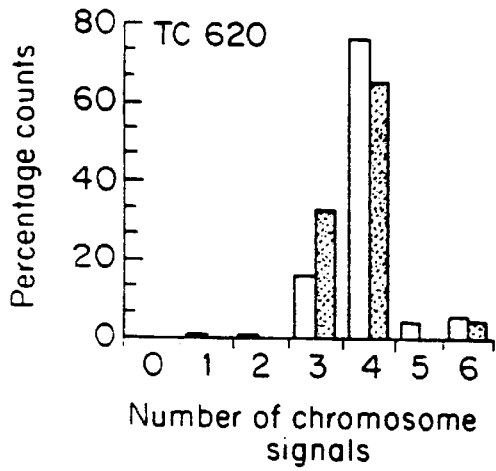
Figure 11C:
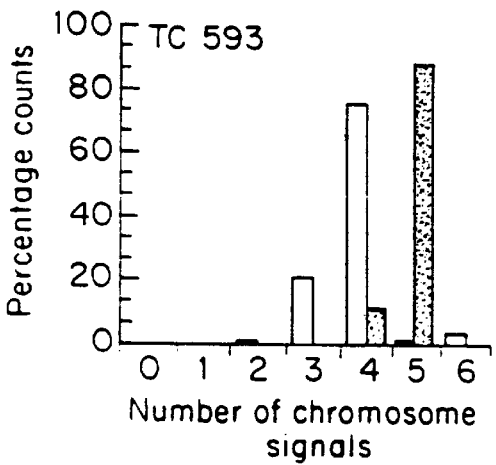

For FIGS. 11A–C: High stringency hybridization (see Materials and Methods) of 7 alphoid repeat was used to avoid cross-hybridization to other chromosomes. In cases of double hybridization with both 7 library inserts and alphoid repeat (shown in FIG. 2 G–I) standard conditions with 50% formamide were sufficient to avoid cross-hybridization, possibly due to the presence of human competitor DNA.

Figure 11D:
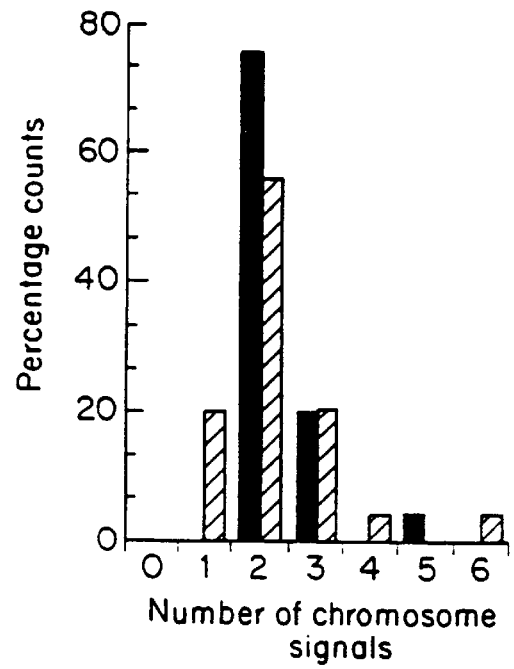

FIG. 11D: Counts of chromosome 22 (library inserts) in metaphase spreads of TC 620 (black columns) and TC 593 (shaded columns). For comparison, CISS hybridization was simultaneously performed with 7 library inserts in these experiments as an internal control (see C, D and FIG. 7).

Figure 11E:
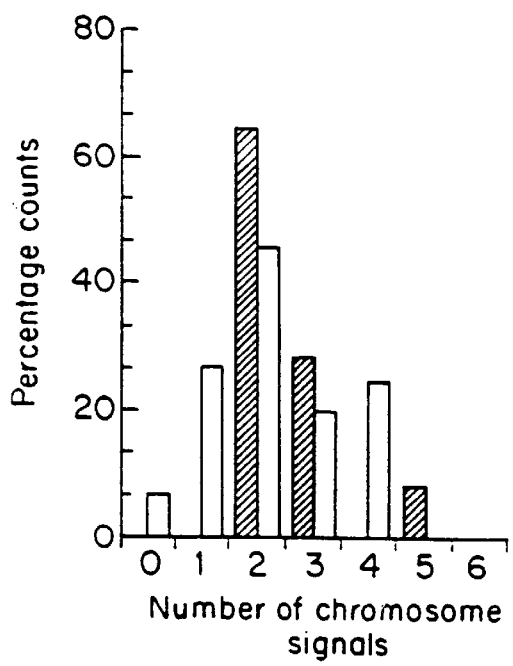

FIG. 11E: Interphase counts (white columns) and metaphase counts (shaded columns) compared in TC 593 hybridized with chromosome 4 inserts. Note the ratio of signal preparations 2:3 are the same in metaphase and interphase.

Figure 12:

FIG. 12 shows a TC 620 metaphase spread after double hybridization with inserts from chromosome 7 and 22 (both labeled with biotin and detected with avidin-FITC). Two strongly decorated 22 chromosomes (arrows), three complete 7 chromosomes and the metacentric marker chromosome containing 7pter-q11 are also seen.

Figure 13:
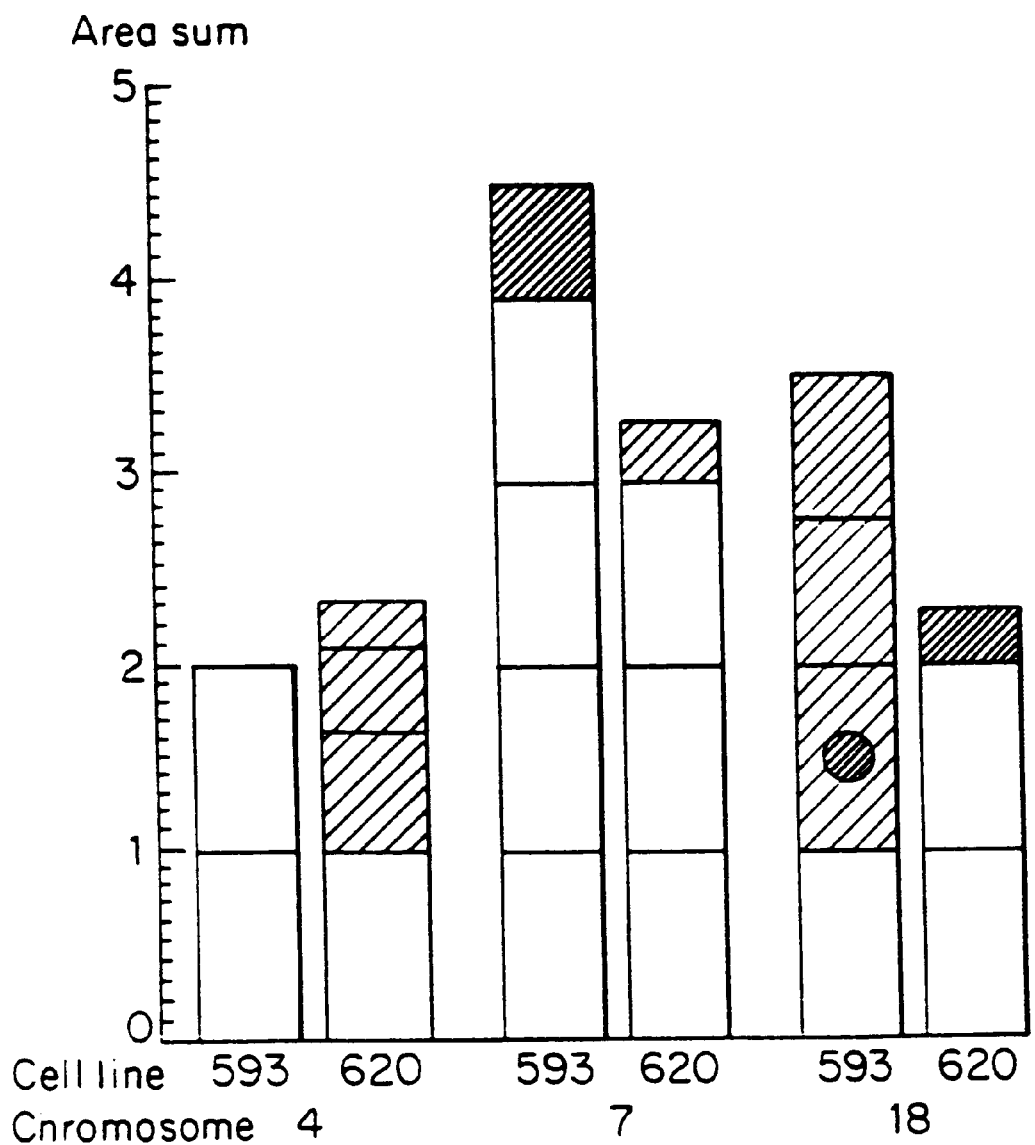

FIG. 13 is a graphic representation of the relative size of decorated normal and aberrant chromosomes 4, 7 and 18 in typical metaphase spreads (n=24) from glioma cell lines TC 593 and TC 620. Individual areas were normalized so that a complete chromosome is represented by an area of 1 (see legend to Table 1). The total added signals reflect the number of specific chromosome equivalents present. The white regions correspond to apparently normal chromosomes, the black regions indicate small free chromosome segments entirely decorated by specific library inserts, and translocated segments are shade. One of the three translocated 18 chromosomes in TC 593 represents a complete chromosome by this measurement (indicated by the black dot), while the two other translocations are slightly smaller, possibly due to the small sample size.

Figure 14A:
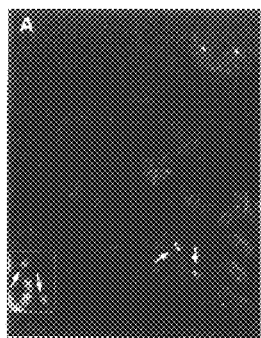

FIGS. 14A–14O show specific labeling of human chromosome 21 by CISS hybridization with biotinylated DNA probe sets.

FIG. 14A: Hybridization of plasmid pPW519-1R (6 kb insert) to a normal lymphocyte metaphase spread. Signals are located on the termini of 21q (see DAPI-stained chromosomes in Inset) as verified by DAPI banding (not shown).

Figure 14B:
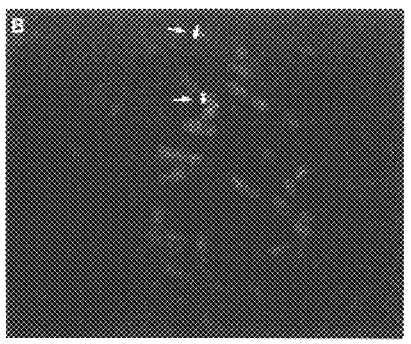

FIG. 14B: Hybridization of the 94 kb plasmid pool probe set to normal human lymphocyte metaphase spread. The terminal band 21q22.3 is specifically labeled.

Figure 14C:
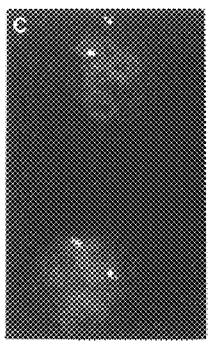

FIG. 14C: The same as for FIG. 14B except that hybridization was to normal human lymphocyte nuclei.

Figure 14D:
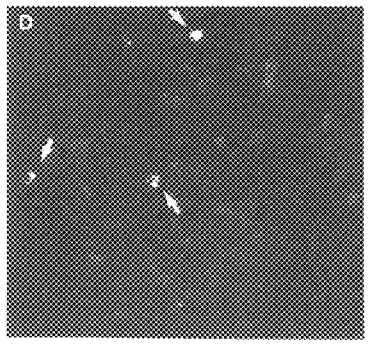

FIG. 14D: Hybridization of the 94 kb probe set to trisomy 21 (47, +21) lymphocyte metaphase spreads.

Figure 14E:
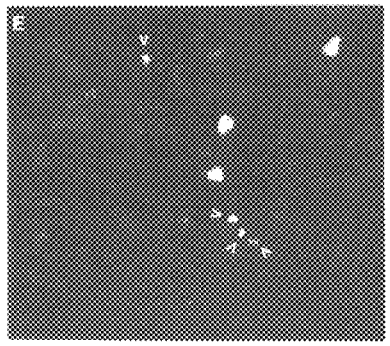

FIG. 14E: Hybridization of chromosome 21 library DNA inserts to trisomy 21 (47, +21) lymphocyte metaphase spreads. Three chromosomes 21 are entirely delineated by the library inserts; additional minor signals (see the text) are indicated by arrowheads (also in FIG. 14G).

Figure 14F:
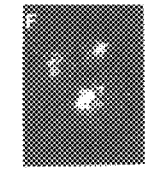

FIG. 14F: Hybridization of chromosome 21 library DNA inserts to trisomy 21 (47, +21) lymphocyte interphase nuclei (compare with 14E).

Figure 14G:
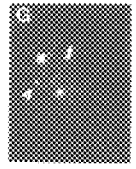

FIG. 14G: Hybridization of chromosome 21 library DNA inserts to trisomy 21 (47, +21) lymphocyte interphase nuclei.

FIG. 14H: Hybridization of chromosome 21 library DNA inserts to trisomy 21 (47, +21) lymphocyte interphase nuclei.

FIG. 14I: Hybridization of chromosome 21 library DNA inserts to trisomy 21 (47, +21) lymphocyte interphase nuclei.

FIG. 14J: Hybridization of chromosome 21 library DNA inserts to trisomy 21 (47, +21) lymphocyte interphase nuclei.

FIG. 14K: Hybridization of the 94 kb probe set to chorionic villi (CV) cell interphase nuclei.

FIG. 14L: Hybridization of the 94 kb probe set to CV cell metaphase spreads.

FIG. 14M: Hybridization of the 94 kb probe set to CV cell metaphase spreads.

FIG. 14N: Hybridization of chromosome 21 library DNA inserts to TC 620 metaphase spread.

FIG. 14O: Hybridization of chromosome 21 library DNA inserts to TC 620 metaphase spreads.

FIGS. 15(A–J) shows hybridization signals from centromeric repeat probes on metaphase chromosomes from a normal male. The labeling combinations used are given in Table 5. The images were taken separately with the appropriate filters and pseudocolored.

(A) Image taken with the fluorescein filter, displaying the fluorescein-11-dUTP-labeled probes for the centromeres of chromosomes 8, 11, 2 and 18. The arrowheads indicate the centromere for chromosome 12, which was singly labeled with fluorescein-dUTP. The arrows show the centromere of chromosome 8, which was labeled with a triple combination.

(B) Detection of the dig-labeled probes with the rhodamine-specific filter. The centromeres of chromosomes 7 (arrowheads), 8 (arrows), 9 and 18 reveal hybridization signals.

(C) Using the infrared filter combination, the biotinylated probes that were detected with streptavidin conjugated to the infrared dye Ultralite 680 are shown. Chromosomes 3 (arrowheads), 8 (arrows), 9 and 11 were detected.

(D, E) Independently acquired gray scale images were merged and pseudocolored, resulting in seven differentially colored centromeric sequences on metaphase chromosomes (D) and in an interphase nucleus (E). DAPI was used as a DNA counterstain.

(F) Example of combinatorial labeling of chromosome-specific libraries with PCR. The libraries for chromosomes 1, 2, 4, 8, 14 and X were labeled singly or combinatorially (see Table 6) and pseudocolored in green, pink, yellow, white, orange and red respectively.

(G) PCR-labeled chromosome-specific libraries were used for detection of a t(2; 14) translocation. The library for chromosome 2 was labeled with biotin and detected with avidin fluorescein; the chromosome 14 library was labeled with dig and detected with anti-dig rhodamine. Both translocation chromosomes are clearly visible (arrowheads).

(H) Combinatorial labeling of cosmid and phage clones by nick-translation. Single gene probes for six different chromosomes were hybridized simultaneously. The probes and the labeling combinations are described in Materials and Methods. Chromosomes 5, 6, 8, 11, 21 and X show hybridization signals.

(I) Combinatorial labeling of six cosmid clones specific for chromosome 5. The differentially pseudocolored probes label six loci on this chromosome simultaneously.

(J) Hybridization of the chromosome 5 specific probes to an interphase nucleus. The order of the cosmid clone is maintained.

DETAILED DESCRIPTION OF THE INVENTION

The present invention is based on a hybridization strategy in which suppression of hybridization signals from ubiqitous repeated DNA sequences is achieved by using total DNA in a reannealing procedure which is based on rapid reassociation kinetics. The hybridization method of the present invention referred to as chromosomal in situ suppression (CISS) hybridization because of the selective suppression of such signals, has been shown to result in specific cyto-staining of one or more selected individual chromosomes, particularly human chromosomes, at any point in the cell cycle and has been used to detect, identify and quantitate chromosomal aberrations in both mitotic cells and interphase cells (i.e., interphase nuclei).

Described below and in greater detail in the Examples, are the following:
1. specific staining in mitotic and interphase cells of individual human chromosomes, by the method of the present invention (CISS hybridization), using chromosome-specific probe sets which are of high genetic complexity (i.e., chromosome library DNA, cloned DNA fragments);
2. specific staining of metaphase and interphase tumor cells by CISS, using chromosome-specific library probes; and
3. rapid detection in mitotic and interphase cells from a variety of sources of aberrations in a human chromosome (chromosome 21) which associated with a genetic condition (Down syndrome), using CISS hybridization.
4. demonstration that a nested set of chromosome specific unique sequence probes used to identify chromosome aberrations and to detect genetic disease (e.g., Down Syndrome).

Specific Staining of Individual Human Chromosomes

Figure 1:
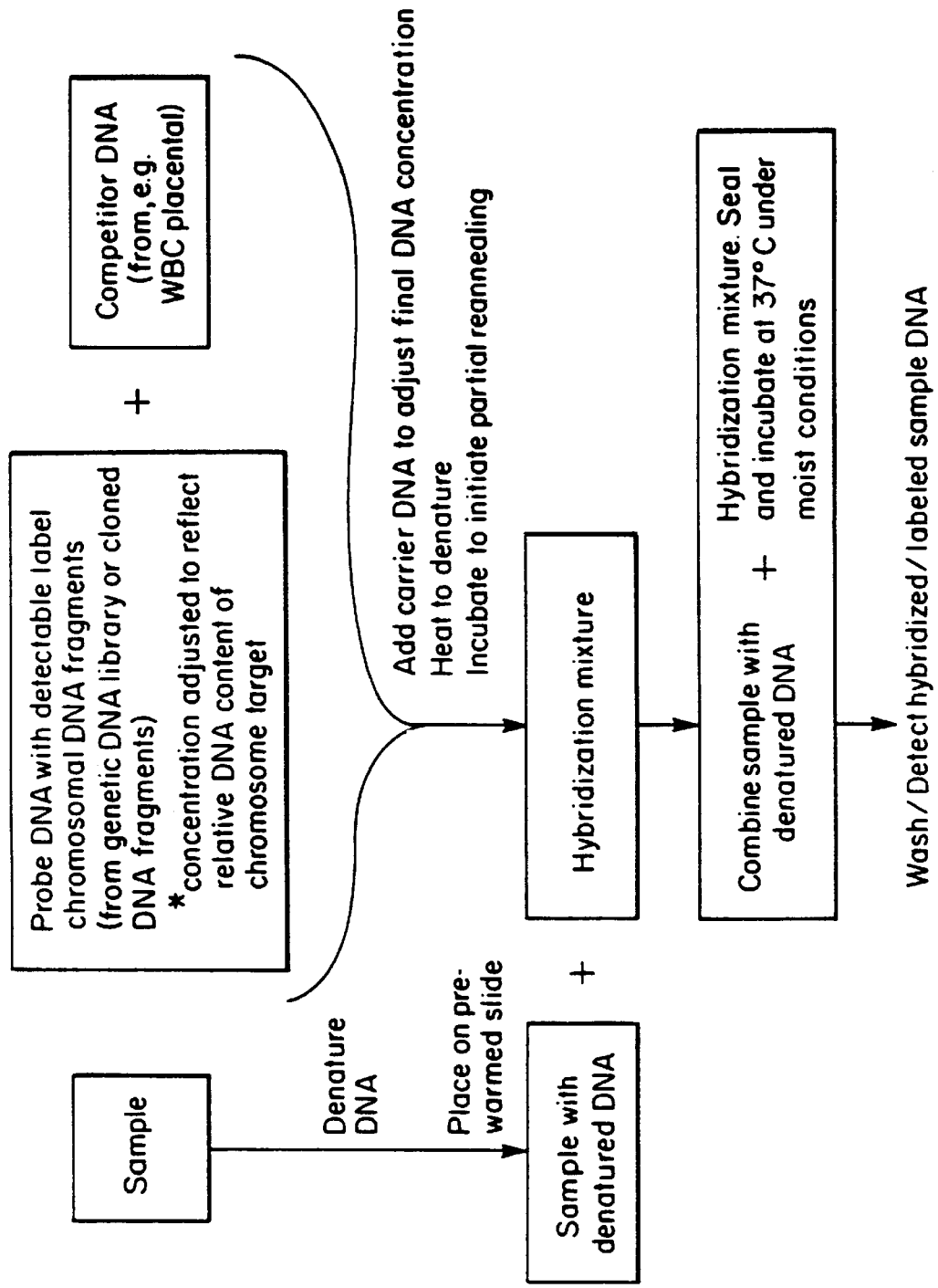
FIG. 1 presents an outline of CISS hybridization for specific staining of human chromosomes.

By use of the CISS hybridization method, individual (such as the X and Y chromosomes or homolog pairs of chromosomes 1–22) human chromosomes have been specifically stained in both mitotic and interphase cells. This has been carried out in both metaphase spreads and interphase nuclei and has been used to stain or label one selected (individual) chromosome and to stain or label multiple selected (individual) chromosomes simultaneously, using, respectively, signal-probe CISS hybridization and multi-probe CISS hybridization in conjunction with an appropriate detection method. The method is represented schematically in FIG. 1.

Specific Chromosome Staining Using Genomic DNA Libraries and Cloned DNA

CISS hybridization was carried out as follows, to produce specific staining of individual human chromosomes, using commercially-available genomic DNA libraries that originated from flow-cytometry sorted human chromosomes and cloned DNA fragments. Van Dilla, M. A. et al., *Biotechnology*, 4:537–552 (1986). Suppression of hybridization signals from ubiquitous repeated sequences, such as the Alu and KpnI elements, was achieved using total human DNA in a reannealing procedure that is based on rapid reassociation kinetics. Similar principles have been used by others to facilitate the selective hybridization of unique sequence subsets from cosmid DNA clones for Southern blotting and in situ hybridization experiments. Sealey, P. G.

et al., *Nucleic Acids*, 13:1905–1922 (1985); and Landegent, J. E. et al., *Hum. Genet.*, 77:366–370 (1987). Specific labeling of individual chromosomes in both metaphase spreads and interphase nuclei, is carried out (and shown to have occurred) in the following manner, which is described in detail in the Examples. The feasibility of using computer-assisted optical sectioning for 3-D reconstruction of chromosomal domains for the analysis of nuclear topography was also demonstrated in conjunction with CISS hybridization.

Initially, genomic DNA from a selected chromosome or selected chromosomes is prepared for use as probe DNA. Genomic DNA is available from several sources. For example, one or more genomic DNA libraries, each containing the chromosome of interest (a chromosome-derived library), is used to produce the necessary DNA probes. Such libraries can be commercially-available genomic DNA libraries that originated from flow-cytometry sorted human chromosomes. These are available from the American Type Culture Collection (Rockville, Md.). Such DNA libraries for human chromosomes 1, 4, 7, 8, 9, 12, 13, 14, 16, 17, 18, 20, 21, 22 and chromosome X have been used in the present method, as described in the Examples. Other commercially available genomic DNA libraries or genomic DNA libraries from noncommercial sources can also be used. Alternatively, individual plasmid, phage, yeast artificial chromosomes with non-yeast DNA inserts, and cosmid DNA clones can be used as a source of DNA probes for a selected individual chromosome or multiple selected chromosomes. In the case of DNA from a genomic library, the DNA can be separated as a pool from the vector containing it, prior to labeling with a detectable signal, or can be used without separation from the vector.

Probes are labeled with a detectable signal, which can be a fluorescent reporter, one member of a specific binding pair (e.g., biotin-avidin or ligand-antibody), or an enzyme. DNA removed from the vector is labeled by nick translation (using, for example, Bio-11-dUTP), by random primer extension with (e.g., 3' end tailing), for example, the Amersham multiprime DNA labeling system, substituting dTTP with Bio-11-dUTP, or other appropriate technique. In the case of DNA which has not been separated from the vector, biotin labeling is carried out directly by nick translation, using standard techniques. Brigati et al., *Virology*, 126:32–50 (1983). Other labels can be added in a similar manner (e.g., 2,4-dinitro phenol, digoxin).

Probe size is carefully selected and controlled in order to facilitate probe penetration and to optimize reannealing hybridization. In general, labeled DNA fragments smaller than 500 nucleotides are used, and, more generally, the majority of the probes are 150–250 nucleotides in length. Probes of this length are made from longer nucleotide sequences using publicly available restriction enzymes or known techniques for producing and recovering appropriately-sized fragments. It is also possible, if the nucleotide sequence of a selected chromosome is known, to synthesize an oligonucleotide having that sequence, using known techniques. Such oligonucleotides, once labeled, can be used to decorate specific chromosomal regions. For example, oligonucleotide probes which specifically hybridize to telomeric sequences of mammalian chromosomes have been identified. Moyuif et al., *Proceedings of the National Academy of Sciences, USA*, September 1988.

Competitor DNA, which is DNA which acts to suppress hybridization signals from ubiquitous repeated sequences, will be selected as needed (e.g., based on the mammal whose chromosomes are being analyzed). In the case of analysis of human chromosomes, competitor DNA is total human DNA which acts to suppress hybridization from ubiquitous repeated sequences, such as the Alu and the KpnI elements. It is available from many sources. For example, human genomic DNA from placenta or white blood cells can be prepared using known techniques, such as that described by Davis et al. Davis, L. G. et al., Basic methods in molecular biology, Elsevier, N.Y./Amsterdam (1986). It is digested, using standard methods (e.g., with DNAse), to produce competitor DNA fragments within the same size distribution as the probe DNA.

DNA from another source, which will compete with only a small portion of the human DNA and which is used, as necessary, to adjust the total (final) DNA concentration of the hybridization mixture will also be included, as needed. This DNA is referred to as carrier DNA. This DNA is produced or treated, using standard methods, so that it is within the same size distribution as the probe DNA.

Initially, probe DNA bearing a detectable label and competitor DNA are combined under conditions appropriate for preannealing to occur. The quantity of probe DNA combined with competitor DNA is adjusted to reflect the relative DNA content of the chromosome target. For example, chromosome 1 contains approximately 5.3 times as much DNA as is present in chromosome 21. Probe concentrations were 30 $\mu$g/ml and 5 $\mu$g/ml, respectively. When total genomic library DNA is used as the probe mixture (instead of purified DNA inserts), approximately 10 times as much labeled DNA is added to compensate for the vector sequences, which are present in large quantities. Only twice as much labeled library DNA is added in the case of the libraries LA0XNL01 (X chromosome) and LA16NL02 (chromosome 16) because the human DNA inserts constitute almost half of the total library DNA. Carrier DNA, such as trout or salmon testis DNA, is added to bring the total DNA concentration to a predetermined level, if necessary. As described herein, sufficient salmon testis DNA was added to result in a final DNA concentration of 1.0 mg/ml in the hybridization mixture (which includes all three types of DNA: probe DNA, competitor DNA and DNA which does not significantly compete).

The resulting hybridization mixture is treated (e.g., by heating) to denature the DNA present and incubated at approximately 37° C. for sufficient time to promote partial reannealing.

The sample containing chromosome DNA to be identified (specifically labeled) is also treated to render DNA present in it available for hybridization with complementary sequences, such as by heating to denature the DNA. The hybridization mixture and the sample are combined, under conditions and for sufficient time conducive to hybridization. After sufficient time, detection of specific labeling of the chromosome target is carried out, using standard techniques. For example, as described in the Examples, a biotinylated probe is detected using fluorescein-labeled avidin or avidin-alkaline phosphatase complexes. For fluorochrome detection, samples are incubated, for example, with fluorescein isothiocyanate (FITC)-conjugated avidin DCS (see Example 1). Amplification of the FITC signal can be effected, if necessary, by incubation with biotinconjugated goat anti-avidin D antibodies, washing and a second incubation with FITC-conjugated avidin. For detection by enzyme activity, samples are incubated, for example, with streptavidin, washed, incubated with biotin-conjugated alkaline phosphatase, washed again and pre-equilibrated (e.g., in AP-buffer, as described in Example 1). The enzyme reaction is carried out in, for example, AP buffer containing nitroblue tetrazolium and 5' oromo 4 chloro 3 indoyl phosphate and stopped by incubation in 2×SSC.

Detection of Chromosome Aberrations Using CISS Hybridization

Using the above-described steps, it is possible to specifically stain or label any selected individual chromosome (or chromosomes) referred to as a target chromosome, or a subregion(s) thereof. As explained in the examples, the present method has been shown to be useful in a variety of cells, both in mitotic (e.g., metaphase, prophase) and interphase cells. As described in detail in Example 2, the CISS hybridization method of the present method is useful for rapidly screening mitotic and interphase aneuploid tumor cells for complex numerical and structural aberrations of individual chromosomes (e.g., changes in number of chromosomes, deletions and rearrangements or translocations).

In this context, biotinylated library DNA inserts were used in the CISS hybridization method to produce hybrid molecules which were detected using known techniques. Two glioma lines were used as general models of aneuploid cells, particularly tumor cells. One was an oligodendroglioma line and the other was a gliobastoma line. These were analyzed, using the biotinylated DNA probes specific for chromosome 1, 4, 7, 18 and 22. Specific labeling of the chromosomes, from pter to qter, made it possible to visualize numerical changes, deletions and rearrangements in these chromosomes in metaphase spreads and in early prophase and interphase nuclei. Complete chromosomes, deleted chromosomes and segments of translocated chromosomes were rapidly delineated in the very complex karyotypes of such cells. Additional subregional probes were also used to further define aberrant chromosomes. Digital image analysis was used to quantitate the total complement of specific chromosomal DNAs in individual metaphase and interphase cells of each line. Under-representation of chromosome 21 and over-representation of chromosome 7 (specifically 7p) were observed. This is in agreement with previous observations by others using conventional cytogenetic bauding techniques. Bigner, S. H. et al., *Cancer Cenet. Cytogenet.*, 22:121–135 (1987); Shapiro, J. R., *Semin. Oncol.*, 13:4–15 (1986).

The two glioma cell lines used display several cytogenetic features common to many glioma cells. Thus, it is reasonable to expect that the CISS hybridization method can be used in a similar manner to specifically decorate other chromosomes and to detect those chromosomes in glial tumors. The two cell types analyzed are highly aneuploid (i.e., they have 100 chromosomes, rather than the normal 46). Therefore, it is reasonable to expect that the CISS hybridization method can be used in assessing any type of aneuploid (tumor) cell.

Thus, the CISS hybridization method can be used in assessing chromosomal aberrations associated with cancer, both in diagnosis of the disease and in monitoring its status (.e.g., progression, regression or change with treatment) in patients. In this application, assessment of a single chromosome or of multiple chromosomes, and subregions thereof, can be carried out. Double hybridizations using two DNA probes, each bearing a different label can also be carried out. That is, biotinylated chromosome 7 library DNA inserts and a probe specific for alphoid repeats on chromosome 7 (pa7t1) which was modified with aminoacetylfluorene (AAF) were used to assess chromosome 7 content/characteristics in both metaphase spreads and interphase nuclei of the two types of tumor cells (TC 593, TC 620). After hybridization, biotinylated chromosome 7 inserts were detected using avidin-FITC and chromosome 7-specific alphoid AAF labeled sequences were detected with tetramethylfhodamine isothiocyanate (TRITC) conjugated second antibodies. Double CISS hybridization was used to detect translation between chromosome 8 and 14, Burkitt lymphoma cells, a high malignancy form of B lymphocyte tumors such were seen in both metaphase spreads and interphase cells.

This made it possible to detect similarities and differences in chromosome number 7 present in the two tumor cell types: only the four complete number 7 chromosomes found in TC 593 contained a detectable 7 centromeric signal; a smaller and metacentric number 7 chromosome lacked the 7 alphoid sequences and a small block of heterochromatin at 7q11 (indicating that it lacked a characteristic centromeric region). In contrast, all four chromosome number 7 of TC 620 were labeled with the 7 alphoid probe. Double CISS hybridization also made it possible to distinguish among number 7 chromosomes present in one cell type (TC 593) and to demonstrate similarity (at least as to the characteristics assessed) among number 7 chromosomes present in the other cell type (TC 620).

Double GISS hybridization was used to detect translocations between chromosome 8 and chromosome 14 in Burkitt's lymphoma cells; Burkitt's lymphoma is a highly malignant form of B lymphocyte tumors. Translocations were detected in both metaphase spreads and interphase cells.

It is possible, through the use of appropriately-selected probes and/or labels to increase the number of different chromosomes, as well as the number of subregions on some or all of those chromosomes, which can be analyzed simultaneously using multiple CISS hybridization. For example, it is possible to use more than one probe, each specific for a subregion of a target chromosome, to analyze several subregions on that single chromosome at one time. It is also possible to label each probe set (set of DNA or RNA fragments) with a distinct fluorochrome or different reporter molecule, which can be distinguished from one another, after probe-target chromosome hybridization has occurred, by known techniques (e.g., by using specific fluorescent or enzyme reagents).

Furthermore, a "combinatorial" variant of CISS hybridization can be used to enhance the number of chromosomes which can be assessed simultaneously. That is, it is possible to use a hybridization probe mixture made from a single set of probe sequences composed of two halves, each separately labeled with a different fluorochrome (e.g., fluorescein and rhodamine), which, upon hybridization, produce a third fluorescence "color" or signal optically distinguishable from each of the original individual fluorochromes. Pairing of two different fluorochromes in this manner makes it possible to identify three different chromosomes. For example, a probe set labeled only with fluorescein will yield one color upon hybridization; the same probe set labeled only with rhodamine will yield a second (different) color upon hybridization. When half of the probe set is labeled with one of the two, both sequence subsets can hybridize to target with equal probability and be perceived as a third (different) color (in a way not dissimilar to mixing paint). It is important here that two fluorochromes are not introduced into the same molecule, in order to minimize the possibility of E transfer (a well-known process where light emitted by one fluorochrome whose spectrum overlaps that of the other fluorochrome is absorbed by the second fluorochrome. The transferred electrons are emitted by second fluorochrome, which leads to quenching of the first fluorochrome. Pairwise combinations of three different fluorochromes selected for their spectral characteristics can be used singly and in pairwise combinations to produce in a similar manner. This can result in the production of six different fluorescent colors or signals (e.g., three pairs plus three single fluorochromes). Similar combinations of four different fluorochromes results in production of 10 different fluorescent colors or signals, of five different fluorochromes results in production of 15 different colors or signals, etc. This principle of combinatorial fluorescence (combining two or more fluorochromes to label the same probe set) is applicable to metaphase and interphase chromosome analysis because each chromosome is a physically separate entity and is, thus, a distinct target. Composite probe labeling in which mixtures of three different fluorochromes are used provides even greater diversity of colors or signals useful in simultaneous multiparameter analysis.

Another approach to enhance the number of chromosomes which can be analyzed simultaneously involves a "time-resolved" method of fluorescence detection. In this instance, the DNA (or RNA) probes are labeled with chelating "cages" which bind specific lanthanides (e.g., Europium, turbium). Such metal chelates can be made to fluoresce. They exhibit excited state lifetimes that are much longer (micro to millisec) than those of most normal fluorochromes (whose half lives are in the nanosecond range). Both the wavelength and the fluorescence lifetime is influenced by the nature of the lanthanide metal ion employed. If a pulsed-gating system, which excites the sample with light for a few nanoseconds and then shuts off is used, it is possible to let short-lived fluorochromes decay to their ground state, open the detector system at a defined time after excitation, (i.e., 1–100 microseconds) and detect only long-lived fluorochrome. This methd can be used to discriminate 2 fluorescent dyes which have identical spectra but different lifetimes, thus adding a time factor to fluorochrome discrimination.

Another approach to increase the number of different chromosomes that can be analyzed simultaneously is based on a detection system which distinguishes chromosomes in terms of the flexibility or rigidity of an attached fluorochrome. Here, two single stranded probe sets can be labeled with the same fluorochrome, in one probe set the fluorochrome is introduced into the body of DNA sequences which will form hybrid molecules with the target DNA of interest. In the second probe set, the fluorochrome is introduced into DNA sequences, that do not hybridize with the target DNA (e.g., by adding a 3'-tail of poly dA-fluorochrome with deoxynucleotide terminal transferase, ligation of fluorochrome-labeled heterologous DNA to the probe DNA or other conventional secondary labeling techniques known in the art). Fluorochromes within the body of the DNA which form probe-target chromosome hybrids will become immobilized and thus will be unable to rotate freely in solution. In contrast, fluorochromes in the single-strand DNA that is not involved in hybrid formation are not immobilized and can rotate much more freely in solution. By measuring the rate of fluorochrome rotational freedom, (i.e., by measuring how fast the fluorochromes become depolarized when illuminated with polarized light) one can discriminate the two sets of probes.

Use of CISS Hybridization and Regionally Defined Probe Sets for Rapid Assessment of Chromosome Aberrations Associated with Genetic Disorders and Chromosomal Damage It has been demonstrated that the CISS hybridization method is useful for the rapid assessment of chromosome aberrations (such as numerical and structural aberrations of chromosome 21) associated with genetic disorders (e.g., in the case of chromosome 21, Down syndrome). DNA probe sets which specifically label the terminal band 21q22.3 or decorate the entire chromosome 21 aberrations in metaphase and interphase cells are described in Example 3, the cloned DNA fragments from the human chromosome 21 are useful to specifically label the cognate chromosomal region in metaphase spreads and interphase nuclei in a variety of cell types. That is, CISS hybridization using a chromosome 21 probe set was shown to be effective in labeling/identifying chromosome 21 DNA in lymphocytes, embryonic chorionic villi cells and a glioma tumor cell line (TC 620). Unique probe sets from band 21q22.3 were also used to detect chromosome solid tissue ("normal" human brain tissue). Thus, CISS hybridization and hybridization with pools of unique sequence probes clearly have potential as a diagnostic for Down syndrome and for other genetic diseases or other conditions associated with chromosomal aberrations.

Results demonstrate that a trisomic karyotype can be diagnosed easily in interphase cells because the majority of the nuclei (55–65%) exhibit three distinct foci of hybridization. In contrast, less than 0.2% of nuclei in lymphocytes with a disomic karyotype show three nuclear signals; interestingly, the percentage of such nuclei in normal CV cells was higher but still considerably less than 5%. In general, as few as 20–30 cells were sufficient to unambiguously distinguish between disomic and trisomic cell populations. However, in view of the uncertainty of the level of chromosome 21 mosaicism in clinical samples, the number of cells required to make an unambiguous diagnosis will likely be higher. Additional clinical correlations will be required to establish the absolute number. Nevertheless, this analytical approach could allow the diagnosis of Down syndrome without the need to culture cells or to obtain metaphase spreads. It would also decrease the time required to make the diagnosis, from the current 10–14 days to 1 day or less.

Although selected plasmid clones containing only unique human DNA sequences were used here, cosmid clones containing repetitive sequences can also be used to specifically label their cognate genomic region in metaphase and interphase cells by applying hybridization protocols like CISS hybridization that suppress the signal contribution of repetitive sequence elements. Therefore, single or nested sets of cosmids could be used as diagnostic tools for other genetic diseases in a fashion similar to that reported here. Trisomy of chromosomes 13, 18 and 21 and numerical changes in chromosomes X and Y together account for the vast majority of numerical chromosome abnormalities identified during prenatal karyotyping. With the continued development of multiple nonisotopic probe labeling and detection systems it should be possible to visualize three or more chromosomes simultaneously following in situ hybridization. The variations, described in the previous section, of the CISS hybridization method which increase the number of chromosomes, and/or the number of chromosome regions which can be assessed simultaneously can also be used for detecting chromosomal aberrations associated with genetic disorders and chromosomal damage. Thus, the development of a rapid and automated screening test to detect the major trisomic disorders directly in interphase cells from amniotic fluid or chorionic villi cells is a viable future objective. The analysis of specific human chromosomes by in situ hybridization has already been used to complement conventional cytogenetic studies of highly aneuploid tumor lines (Example 2) and the extension to prenatal diagnostic applications seem warranted.

The analysis of karyotypes with translocations of chromosome 21 shows the usefulness of a regional probe set to rapidly identify and characterize even small translocations by unambiguous signals on metaphase chromosomes, thus circumventing an extensive analysis by high-resolution banding. In contrast, the library insert probe is more suitable for defining the relative amount of chromosome 21 DNA that has been translocated. By analyzing interphase nuclei, one can also determine if a balanced or unbalanced number of chromosomal regions exists. However, the detection of a translocated chromosome directly in nuclei would require doublelabeling techniques to identify the recipient chromosome to which the chromosome 21 material was translocated. With prior knowledge of the chromosome in question, such translocation events could be assessed by measuring the juxtaposition of the nuclear signals. Rappold, G. A. et al., *Hum. Genet.*, 67:317–325 (1984).

A cosmid clone spanning the entire muscular dystrophy (MD) locus on chromosome X has been used to identify translocation between chromosome X and chromosome 4.

Probes containing 6 kb of sequence were localized in both metaphase spreads and interphase cells with high efficiency. This detection sensitivity with nonisotopic reagents is similar to that achieved in other recent reports. The combination of nonisotopic in situ hybridization with DAPI or BrdUrd banding or total chromosome decoration with library DNA probes thus provides a simple and general approach for gene mapping. Combinatorial fluorescent technology will also make it possible to examine several chromosomal regions simultaneously, thus permitting genetic linkage analysis by in situ hybridization. It also should facilitate the use of small DNA probes to rapidly pinpoint the breakpoints on translocation chromosomes, which could further aid in defining the genomic segments critical for Down syndrome.

Identifying an Isolating Chromosome-Specific Sequences Using CISS Hybridization

The CISS hybridization method of the present invention can also be used to identify chromosome-specific sequences and, subsequently, to separate them from repetitive sequences, using known techniques. Such chromosome-specific sequences, separate from the non-specific or repetitive sequences, and labeled, can be used in hybridization assays carried out, for example, in a diagnostic context, to identify, detect, and/or quantitate a chromosome or chromosome region of interest (e.g., one which is associated with a genetic disorder or causes an infectious disease). Combination of a sample to be assayed for a selected target nucleic acid sequence or sequences and appropriately-selected, labeled chromosome-specific sequences separated from repetitive sequences (e.g., sequences specific for sequences on the chromosome(s), generally referred to as target nucleic acid sequences, which are to be detected and/or quantitated in the sample under appropriate conditions results in hybridization with complementary sequences present in the sample. Hybridization will not occur, of course, if complementary sequences are not present in the sample.

Such separated chromosome-specific nucleic acid sequences can be incorporated into a kit to be used for identification, detection and/or quantitation of chromosomes or chromosome regions of interest, using standard hybridization techniques. For example, labeled nucleic acid sequences which are chromosome 21 specific (or specific to a portion of chromosome 21), identified by CISS hybridization, and separated from repetitive sequences present on chromosome 21, can be included in a kit, along with other reagents such as buffers, competitor DNA, carrier DNA and substances needed for detection of labeled chromosome 21-derived nucleic acid sequences hybridized to chromosome 21 sequences present in a sample. Such kits clearly can be produced to include chromosome-derived nucleic acid sequences from one or more chromosome(s) of interest. Competitor DNA, carrier DNA and substances useful for detecting hybridized sequences will be as described above.

EXAMPLE 1

Cyto-Specific Staining of Individual Human Chromosomes Using Genomic DNA Libraries in CISS Hybridization DNA Libraries The following human chromosome genomic libraries were obtained from the American Type Culture Collection: LA01NS01 (chromosome 1), LL04NS01 (chromosome 4), LA07Ns01 (chromosome 7), LL08NS02 (chromosome 8), LA13NS03 (chromosome 13), LL14NS01 (chromosome 14), LL19NS01 (chromosome 18), LL20NS01 (chromosome 20), LL21NS02 (chromosome 21), LA22NS03 (chromosome 22), LA0XNL01 (chromosome X). Amplification of these phage libraries on agar plates (using LE 392 cells as the bacterial host), purification of the λ phages and extraction of phage-DNA pools were carried out according to standard protocols. Maniatis, T. et al., Molecular Cloning: A Laboratory Manual, Cold Spring Harbor Laboratory, Cold Spring Harbor, N.J. (1982).

Preparation of Metaphase Spreads and Fibroblast Cells

Phytohemagglutinin-stimulated lymphocytes from a normal adult male (46, XY) were cultured in McCoy's 5A medium (GIBCO), arrested with Colcemid, treated with a hypotonic solution of 0.075 M KCl, fixed in acetic acid-methanol and metaphase spreads made by standard procedures. Low-passage normal human foreskin fibroblasts (46, XY) were grown on microscope slides, fixed with paraformaldehyde, and permeabilized as described for study of preparations with a more intact three-dimensional structure. Manuelidis, L, *Ann. NY Acad. Sci.*, 450:205–221 (1985).

Preparation of DNAs for in Situ Hybridization

Insert DNA probes. Genomic DNA fragments from the chromosomal DNA libraries were separated as a pool from the Charon 21A vector arms by digestion with the appropriate restriction enzyme [EcoRi (LA libraries) or Hind III (LL libraries)], followed by preparative electrophoresis in 0.6% agarose gel. The insert fragments were isolated from gel slices by electroelution into an Elutrap (Schleicher and Schuell) and further purified by Elutip-d column chromatography (Schleicher and Schuell). The DNA was then extracted with phenol/chloroform (1:1) and ethanol precipitated. This pool of DNA fragments was labeled either by nick translation using Bio-11-dUTP or by random primer extension with the multiprime DNA labeling system (Amersham) substituting dTTP with 0.5 mM Bio-11-dUTP. Langer, P. R. et al., *Proc. Natl. Acad. Sci. USA*, 78:6633–6637 (1981) and Brigati, D. J. et al., *Virology*, 126:32–50 (1983). Alternatively, the DNA of the chromosome-specific libraries was biotin-labeled directly (without separation of the vector arms) by nick translation.

Probe size. To facilitate probe penetration and to optimize reannealing hybridization, it is desirable to have labeled DNA fragments smaller than 500 nucleotides; the majority of the probes are generally 150 to 250 nucleotides in length. DNAse concentrations were empirically established in nick-translation reactions to yield fragments in the desired size range and this was verified by agarose gel electrophoresis. Random primer extensions were also carried out under conditions which yielded a comparable DNA size distribution.

Competitor DNA. Human genomic DNA (from placenta or white blood cells), prepared as described, as well salmon testis genomic DNA (Sigma) were digested with DNAse to obtain fragments with the same size distribution as the probe DNA, then extracted with phenol/chloroform and ethanol precipitated. Davis, L. G. et al., "Basic methods in molecular biology", Elsevier, New York Amsterdam (1986). These competitor DNAs were used in varying ratios with probe sequences, as described with reference to FIGS. 2A–2F.

Preannealing and hybridization. Under standard conditions, from 5 μg/ml to 30 g/ml of biotin-labeled DNA, representing library insert fragments, and varying amounts of competitor DNAs were combined, ethanol-precipitated and resuspended in formamide. The probe concentration was adjusted to reflect the relative DNA content of each chromosome target. For example, chromosome 1 contains approximately 5.3 times as much DNA as chromosome 21; thus the probe concentrations used were 30 μg/ml and 5 μg/ml, respectively. Mendelsohn, M. L. et al., *Science*, 179:1126–1129 (1973). When total library DNA was used as the probe mixture instead of purified DNA inserts, 10 times as much labeled DNA was added to compensate for the large amount of vector sequences. In the case of the X-chromosome library, LA0XNL01, only twice as much labeled library DNA was used, since the human DNA inserts constitute almost half of the total DNA. For comparative purposes, the concentration of human competitor DNA in the hybridization mixture was varied from 1 to 1.0 mg/ml and salmon testis DNA was added as required to result in a final DNA concentration of 1.0 mg/ml in 50% formamide, 1×SSC (0.15 M sodium chloride, 0.015 M sodium citrate, pH 7.0) and 10% dextran sulfate. These solutions were heated at 75° C. for 5 min. to denature the DNA and then incubated at 37° C. for various times to promote partial reannealing. The preannealing step was done in an Eppendorf tube just prior to applying the hybridization mixture to the specimen. Nuclei and chromosome spreads on glass slides were incubated in 70% formamide, 2×SSC] at 70° C. for 2 min. to denature chromosomal DNA and then dehydrated in a series of ice-cold ethanal (70%, 90% and 100%, each for 3 min.). After application of the preannealed probe mixture (2.5 μl/cm$^2$) to slides prewarmed to 42° C., a coverslip was added and sealed with rubber cement. The samples were then immediately incubated at 37° C. in a moist chamber for 10–20 h.

In those cases where paraformaldehyde fixation was used to more optimally preserve the 3-D structure of the specimen, the slides were equilibrated in 50% formamide, 1×SSC (2×5 min.), excess fluid was removed without permitting the sample to dry, the probe mixture was added (5 μm/cm$^2$), and a coverslip mounted and sealed with rubber cement. Manuelidis, L., *Ann. NY Acad. Sci.*, 450:205–221 (1985). Denaturation of both probe and cellular DNA was done at 75° C. for 5 min. before hybridization was allowed to proceed overnight at 37° C.

Detection

After hybridization, the slides were washed in 50% formamide, 2×SSC (3×5 min., 42° C.) followed by washes in 0.1×SSC (3×5 min., 60° C.). Thereafter the slides were incubated with 3% bovine serum albumin (BSA), 4×SSC for approximately 30 minutes at 37° C. Detection of the biotinylated probe was achieved using either fluorescein-labeled avidin or avidin-alkaline phosphatase complexes. All detection reagents were made up in 4×SSC, 0.1% Tween 20, 1% BSA and all washes were carried out in 4×SSC, 0.1% Tween 20 (3×3 min., 42° C.). For fluorochrome detection, slides were incubated with 5 μg/ml fluorescein isothiocyanate (FITC)-conjugated avidin DCS (Vector Laboratories) at 37° C. for 30 min., followed by washes. In rare cases, the FITC signal was amplified by incubation with 5 μg/ml biotin-conjugated goat anti-avidin D antibodies (Vector Laboratories) at 37° C. for 30 min., followed by washing, a second incubation with 5 μg/ml FITC-conjugated avidin (37° C., 30 min.) and a final wash. Pinkel, D. et al., *Proc. Natl. Acad. Sci. USA*, 83:2934–2938 (1986). For detection by enzyme activity, samples were incubated with 2.5 μg/ml streptavidin, washed, incubated with 2 μg/ml biotin-conjugated alkaline phosphatase (Vector Laboratories), washed again and pre-equilibrated in Ap-buffer 9.5 (100 mM Tris-HCl, pH 9.5, 100 mM NaCl, 50 mM MgCl$_2$) for 2×5 min. at room temperature. The enzyme reaction was carried out in AP buffer 9.5 containing 330 μg/ml of nitroblue tetrazolium (NBT) and 165 μg/ml 5-bromo-4-chloro-3-indolyl phosphate (BCIP) at 37° C. for 0.5–1 hour and stopped by incubation in 2×SSC. All preparations were counter-stained with 200 ng/ml 4,6-diamidino-2-phenylindole-dihydrochloride (DAPI), 2×SSC for 5 min. at room temperature and mounted in 20 mM Tris-HCl, pH 8.0, 90% glycerol containig 2.3% of the DAPCO antifade, 1,4 diazabicyclo-2(2,2,2)octane. Johnson G. D. et al., *J. Immunol. Methods*, 55:231–242 (1982).

Densitometry

A graphics workstation (VAX station II/GPX, Digital Equipment Corporation) with a frame grabber (ITEX FG-101, Imaging Technology) and a Dage-MTI-65 video camera with a Zeiss S-Planar 60 mm lens were used as described in Manuelidis, L. and J. Borden, *Chromosoma*, 96:397–410 (1988). Images were digitized directly from the negatives and stored on disk. Background was removed and polygonal regions around each chromosome were defined. Threshold density levels were used to outline chromosome regions within the defined polygonal areas. Means density levels within these outlined chromosome regions, R, were determined by the total signal $\int I(x,Y)dR$/area R, where $\int I(x,y)$ is the pixel intensity (0–225) at each point within the region R. The threshold background intensity was substrated from the mean regional density, both for labeled chromosome 7 and for background chromosomes. The signal to noise ratio was calculated as mean chromosome 7 signal/ mean background chromosome signal.

The following is a description of the results of the work described above, which clearly demonstrate specific labeling of the individual chromosome indicated. The first sections describe use of chromosome library inserts labeled with biotin and the second describes use of DNA insert fragments.

FIGS. 2A–2F show suppression of signals from cross-reacting sequences within a chromosome 7-derived DNA library by different concentrations, as described below.

Figure 2A:
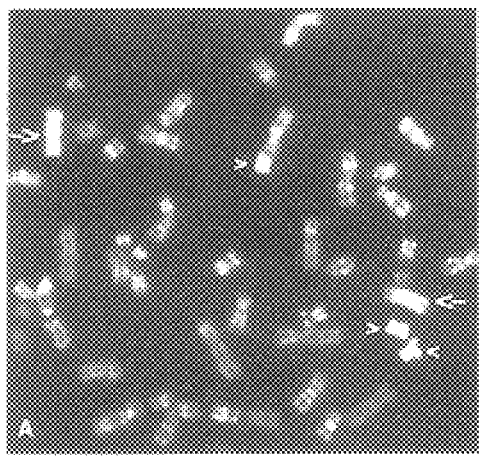
FIGS. 2A–2F show suppression from cross-reacting sequences within a chromosome 7-derived DNA library by different concentrations of human competitor DNA. Biotin-labeled chromosome 7 DNA inserts (20 $\mu$g/ml) were prehybridized for 20 minutes with human genomic DNA prior to hybridization with metaphase chromosome spreads and detection wit FITC-labeled avidin. Genomic salmon DNA was added to each sample to adjust the final DNA concentration to 1.0 mg/ml (see the text for details). The arrows mark the target chromosome 7 and the arrowheads mark additional strong signals on non-7 chromosomes. All negatives printed were exposed and developed under identical photographic conditions.

FIG. 2A shows chromosome 7 library inserts labeled with biotin and hybridized to metaphase spreads from normal human lymphocytes without human competitor DNA. Prominent labeling of the two no. 7 chromosomes is observed; additionally, a distinct band-like patterns of hybridization is seen on most of the other chromosomes, and two E-group chromosomes are especially brightly stained. This general chromosomal banding pattern resembles R-banding, and suggests that a significant portion of the background cross-hybridization signal originates from Alu repetitive sequences. Previous studies have shown that Alu sequences delineate an R-banding pattern, while Giemsa positive-banding profiles are highlighted by KpnI interspersed repeats. Manuelidis, L. and C. D. Ward, *Chromosoma*, 91:28–38 (1984).

Establishment of Experimental Procedure to Eliminate the Hybridization Signal from Repetitive Elements A series of pilot studies were therefore undertaken to establish experimental parameters to eliminate the hybridization signal from such repetitive elements. The kinetics of nucleic acid reassociation in solution are dependent on the total concentration of nucleic acid (Co, in moles of nucleotides per liter) and the time of renaturation (t, in seconds). When reassociation conditions are standardized for temperature (taking into account the formamide concentration), cation concentration and buffer system, the reassociation kinetics are comparable with respect to Cot values. Under defined conditions, the fast reassociating fraction of mammalian genomes containing the highly repetitive DNA is completely reannealed at Cot values between $1 \times 10^{-1}$ and $5 \times 10^{-1}$; the intermediate fraction containing the middle repetitive DNA is completely renatured at a Cot value of $1 \times 10^0$ Britten, R. J. and D. E. Kohne, Science, 161:529–540 (1968). Thus at a human DNA concentration of 1.0 mg/ml (corresponding to $3 \times 10^{-3}$ moles of nucleotide per liter), the fast fraction would be renatured in approximately 10s, whereas the middle repetitive DNA would need more than 9 h to reach complete reannealing. Since the fast fraction of reassociating DNA containing most or all of the ubiquitous repetitive DNA causing cross-hybridization signals, a total DNA concentration of 1.0 mg/ml was used and partial reannealing of the probe mixture was allowed prior to application to specimens. The optimal renaturation time was determined empirically (see below). This was important because the in situ hybridization conditions deviate from the standard conditions under which reassociation kinetics are determined (e.g., hybridization in 50% formamide at 37° C. corresponds to 0% formamide at about 70° C.; dextran sulfate also increases the reassociation time significantly). Furthermore, it was unclear to what degree the middle repetitive DNA contributed to the non-specific signal and therefore should also be prevented from hybridization by a preannealing procedure.

The stringency for the reannealing and in situ hybridization experiments was determined in 50% formamide at 37° C. (adapted from standard in situ hybridization protocols) and 1×SSC [this cation concentration of 0.165 M comes close to the concentration used in the kinetics study of Britten and Kohne. Britten, R. J. and D. E. Kohne, *Science*, 161:529–540 (1968)]. Competitor human DNA was added in the reassociation procedure to obtain the desired final high DNA concentration and to maintain a high level of repetition of the DNA sequences that should preanneal. While total human genomic DNA represents all the highly repetitive DNA to be removed by preannealing, it also contains sequences of the target chromosome. Thus, the addition of excessive amounts of human DNA would be expected to diminish the chromosome-specific signal. Therefore, the optimal concentration of total human DNA to use as the competitor was first determined. To keep the total DNA concentration constant at 1.0 mg/ml, genomic salmon DNA was added as needed. Salmon DNA shares certain repetitive DNA elements, such as poly dCdA in common with human DNA, but lacks others, most notably the Alu- and KpnI repeats. Hamada, H. et al., *Proc. Natl. Acad. Sci. USA*, 79:6465–6469 (1982). This results in a lower frequency of the latter sequences with increasing amounts of salmon DNA in the reassociation reaction.

Figure 2B:
Figure 2C:
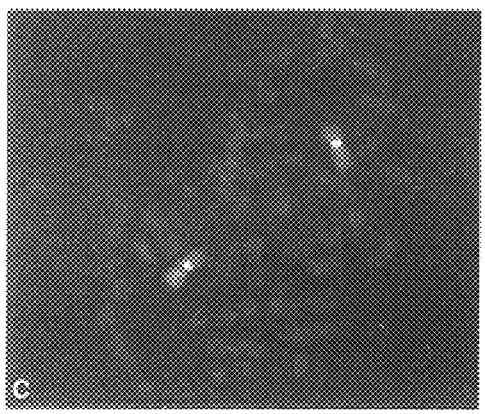
Figure 2D:
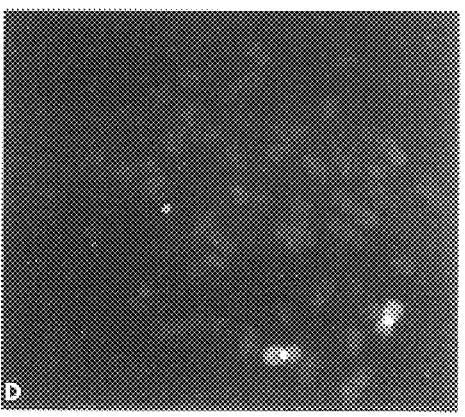
Figure 2E:
Figure 2F:
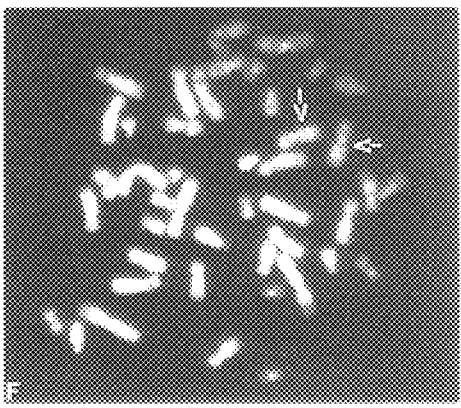

FIGS. 2A–2F show typical experimental results obtained when 20 μg/ml of the chromosome 7 probe set was denatured together with 50 μg/ml (FIG. 2B), 100 μg/ml FIG. 2C, 200 μg/ml FIG. 2D or 1000 μg/ml FIG. 2E of DNAse-digested human genomic DNA which was preannealed for 20 min. Hybridization and detection using avidin-FITC were carried out as described above. From each preparation ten black and white pictures were taken under standardized photographic conditions for densitometric studies (see below). In the absence of human genomic competitor FIG. 2A the signal showed little chromosomal specificity. However, with 50 and 100 μg/ml of human competitor DNA, as increase of label specificity is readily apparent (FIGS. 2B, C). Specific staining of chromosome 7 was achieved with a peak of signal intensity using 100 and 200 μg/ml of human competitor DNA (FIGS. 2C, D). Higher concentrations of human DNA caused an apparent decrease of signal intensity, especially at 1000 μg/ml human DNA (FIG. 2E). However, the signal obtained under these latter conditions is still reasonably bright to the observer, but requires a different exposure for optimal illustration (not shown).

A computer-assisted method of quantitative densitometry (see above) was used to establish the overall level of labeling specificity. The ratio of fluorescence signal from the target chromosomes of interest to the background fluorescence noise emanating from non-target chromosomes was determined from images digitized from multiple photographic negatives of a DNA titration experiment, as illustrated in FIGS. 2A–2F. The signal-to-noise ratio obtained with each concentration of human competitor DNA is given in Table 1.

TABLE 1

Densitometric analysis of the suppression of cross hybridization signals by concentrations of human competitor DNA

| DNA conc. μg/ml) Human competitor | Signal | | Noise | | Signal-to-noise ratio Confidence interval[c] |
|---|---|---|---|---|---|
| DNA conc. | Pixel[a] | η | Pixel[b] | η | (99%) |
| 0 | 71.48 | 8 | 54.66 | 26 | 1.31 ± 0.04 |
| 50 | 74.50 | 8 | 37.43 | 28 | 1.99 ± 0.07 |
| 100 | 162.64 | 8 | 20.06 | 23 | 8.11 ± 0.35 |
| 200 | 147.35 | 8 | 20.53 | 26 | 7.18 ± 0.37 |
| 500 | 89.78 | 8 | 18.63 | 21 | 4.82 ± 0.28 |
| 1000 | 94.37 | 8 | 30.51 | 17 | 3.09 ± 0.12 |

[a]Mean value of pixel intensity of target chromosome
[b]Mean value of pixel intensity of non-target chromosomes (from the same metaphase spreads)
[c]The confidence interval was calculated using Fieller's theorem (Finney, D.J., Statistical methods in biological assay, 2nd edn., Hafner Press, N.Y., 1971)
η Number of chromosomes from which the mean was determined Optimal reannealing conditions for suppression of nonspecific signal (using 20 μg/ml of chromosome 7 probe and 100–200 μg/ml human genomic (DNA), gave a signal-to-noise ratio of ca. 8:1. Additional attempts to improve the signal to noise ratio by increasing hybridization stringencies (e.g., 60% formamide or 0.2×SSC) gave no apparent improvement and led to an overall decrease in signal intensity.

Since about 100–200 μg/ml of human competitor DNA was shown to give the optimal specificity, 200 μg/ml was used for another analysis of signal specificity with respect to the renaturation time (see above). After 0, 2, 5, 10, 20, 40 and 50 min. of preannealing, aliquots were taken and used for in situ hybridization experiments as before. As indicated in FIGS. 3A–3D, specific labeling was obtained for all preannealing times. A small improvement of the signal is seen with increasing renaturation times from 0 to 20 min.

Longer renaturation times up to 60 min. (not shown) gave no significant improvement in signal strength or chromosome specificity. The subjective impression of a signal improvement with 20 min. of preannealing (FIG. 3D) could not be confirmed by a densitometric analysis, carried out as described above, since no significant differences in the signal-to-noise ratio of the different preannealing times were observed (data not shown). Therefore, the standard renaturation time in all subsequent experiments was 10–20 min. Since a signal is clearly visible at renaturation time 0, the few seconds necessary for transferring the probe mixture to the microscope slide appear to be sufficient to effectively preanneal many of the sequences that cause nonspecific labeling by cross-hybridization. Furthermore, the large excess of single-stranded competitor DNA may efficiently compete with the biotinylated probe sequences for ubiquitious chromosomal target sites during the hybridization reactions. These results demonstrate that the majority of highly repetitive DNA sequences can be sufficiently suppressed to achieve chromosome-specific labeling by in situ hybridization.

Figure 4A:
FIG. 4A show decoration of chromosome 1 in normal human lymphocytes. The signal of chromosome 1 was amplified by the sandwich technique of Pinkel et al. (1986).
Figure 4B:
FIG. 4B shows decoration of chromosome 7 in normal human lymphocytes.

In certain cases the signal distribution over the entire chromosome shows some variability from experiment to experiment. When the overall signal is decreased, some chromosomal subregions show a brighter staining; these signal hotspots generally constitute chromosomal sites that contain known chromosome-specific repetitive sequences. In the experiments shown in FIGS. 2A–2F and FIGS. 3A–3D, predominent staining of the centrometric region of chromosome 7 is seen, which corresponds to the chromosomespecific signal of an alphoid repetitive DNA. Waye, J. S. et al., *Mol. Cell Biol.*, 7:349–356 (1987) and see Example 2. Apparently, the abundance of these repeated sequences is sufficiently low to prevent their suppression under the conditions used here. The unequal signal distribution can be overcome by amplifying the overall signal using an antibody sandwich technique as described above. Furthermore, a predominant staining of the region 1q12 that corresponds to the chromosomal site of satellite III DNA was frequently observed in labeling chromosome 1. Cooke, H. J. and J. Hindley, *Nucleic Acids Res.*, 6:3177–3197 (1979) and Cosden, J. R. et al., *Cytogenet. Cell Genet.*, 29:32–39 (1981) and see Example 2. An example of the balanced signal distribution seen after such an amplification step is shown in FIG. 4A.

Several commercially available DNA libraries, each representing a single human chromosome, were tested for their ability to specifically label the chromosome they represented, under the standardized reannealing conditions described above and with the probe concentrations adjusted for chromosome size, as described above. Some examples, for chromosomes 1, 4, 7, 13, 18 and 20, as shown in FIGS. 4A, 4B, 4C, 4D, 4E and 4F clearly demonstrate that specific labeling can be achieved with most chromosome libraries. Table 2 lists the libraries tested with their relative scores of labeling specificity. All scores are positive because the chromosome of interest was always decorated. The highest score (4+) is used when no significant cross-hybridization to other chromosomes was observed and the scores decrease (3+ to 1+) with an increasing amount of cross-hybridizing sequences.

TABLE 2

Relative quality of specific chromosome labeling in situ using preannealed biotinylated library DNA inserts

| Chromosome | Library used (ATCC designation) | Relative specificity of in situ hybridization signal[1] |
|---|---|---|
| 1 | LA01NS01 | 3+ |
| 4 | LL04NS01 | 4+ |
| 7 | LA07NS01 | 4+ |
| 8 | LL08NS02 | 4+ |
| 13 | LA13NS03 | 1+ |
| 14 | LL14NS01 | 2+ |
| 18 | LL18NS01 | 4+ |
| 20 | LL20NS01 | 4+ |
| 21 | LL21NS02 | 3+ |
| 22 | LA22NS03 | 3+[b] |
| X | LA0XNL01 | 4+ |

[a]See the text for score definition
[b]Under standard preannealing conditions the chromosome 22 library gave a score of +1; a value of +3 was achieved only with a human competitor DNA concentration ≧700 μg/ml (total DNA concentration 1.0 mg/ml).

All attempts to reduce the additional signals on chromosomes by varying the experimental conditions failed except in experiments with chromosome 22; in this case higher concentrations of human competitor DNA (700 μg/ml) resulted in a significant improvement of signal specificity. The library exhibiting the lowest chromosome specificity was the chromosome 13 library (FIG. 4E). Multiple minor binding sites on other chromosomes, as well as an exceptionally bright staining of Yq12 were observed; the signal on the Y chromosome was visible using either female or male human DNA as the competitor. None of the experimental parameters tested improved on the overall specificity of this library.

Figure 4C:
FIG. 4C shows decoration of chromosome 4 in normal human lymphocytes.
Figure 4D:
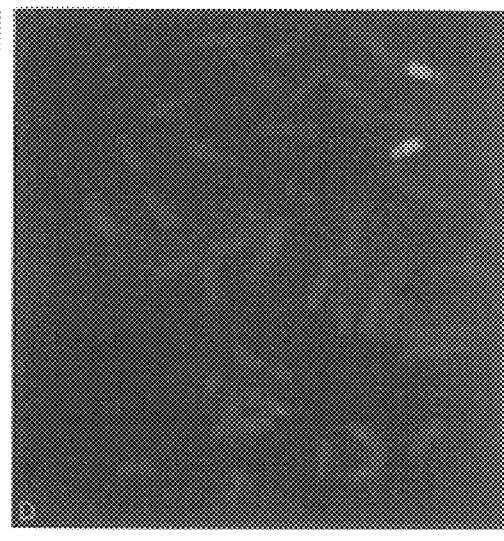
FIG. 4D shows decoration of chromosome 18 in normal human lymphocytes.
Figure 4E:
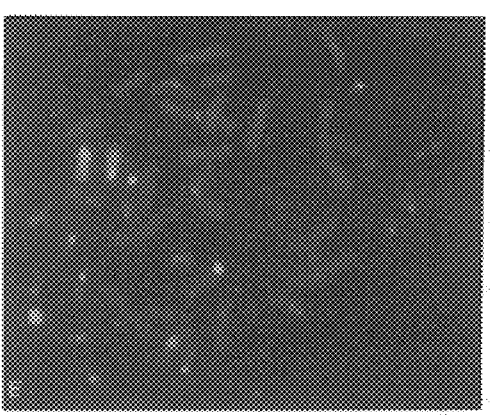
FIG. 4E shows decoration of chromosome 13 in normal human lymphocytes. Only the chromosome 13 insert DNA pool shows significant cross-hybridization to other chromosomes after the prehybridization suppression step.

Remarkably, a weak signal or even absence of signal can be observed at the centromeric region of some chromosomes (see chromosomes 4 and 18, FIGS. 4C, D). In contrast to chromosomes 1 and 7, which contain chromosome-specific repetitive elements, the centromere regions of chromosomes 4 and 18 apparently contain repetitive sequences, most likely alphoid satellite DNAs, which are very abundant and thus are suppressed by the reannealing technique. However, these chromosomal regions are very small and the effect can only be observed when the corresponding chromosomes are fairly elongated.

Figure 4F:
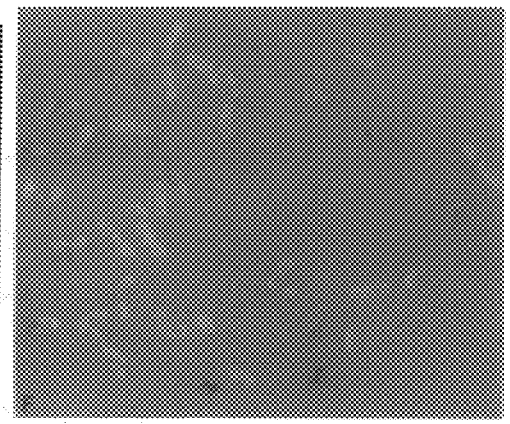
FIG. 4F shows decoration of chromosome 20 in normal human lymphocytes. The detection of chromosome 20 was done with the entire chromosome library (including λ phage arms) and detected with avidin-alkaline phosphatase using nitro blue tetrazolium/5-bromo-4-chloro-3-indolyl phosphate (NBT-BCIP) as the enzyme substrate mixture.
Figures 5A, 5B, 5C, 5D, 5E, 5F:
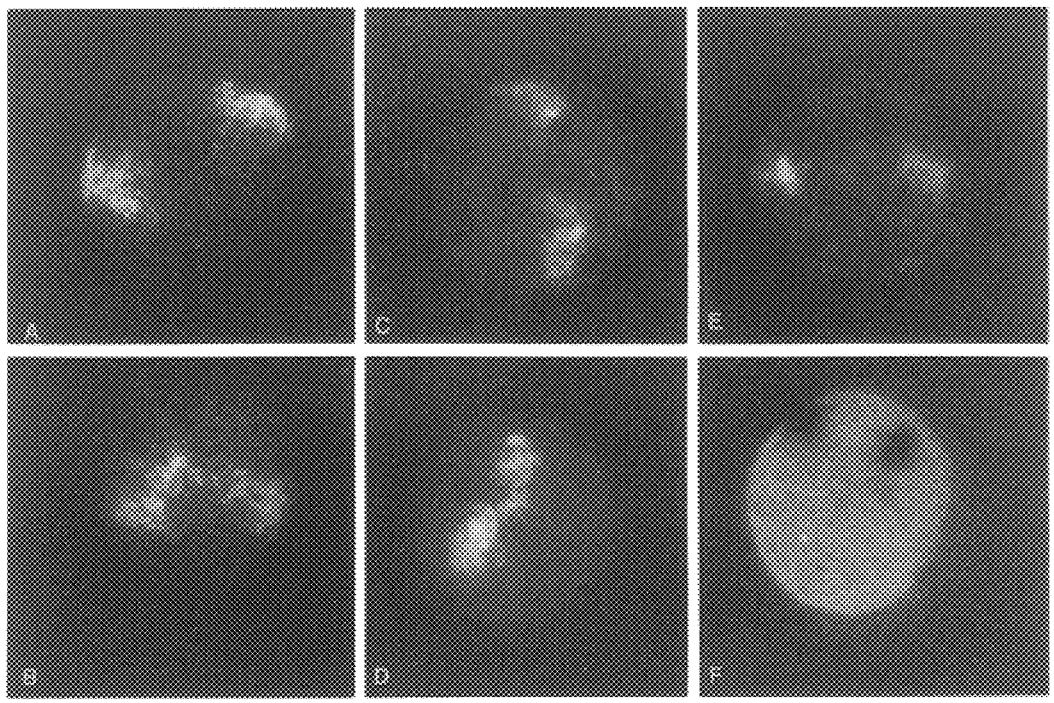
FIGS. 5A–5F show chromosome domains in human lymphocyte nuclei delineated by preannealed chromosome library DNA inserts.

Biotinylated total library DNA (containing the phage vector sequences) was also used as probes, in concentrations adjusted to the amount of human DNA inserts. (see above). One example is shown in FIG. 4F with the chromosome 20 library. Although good staining of the chromosome of interest generally was achieved, significant nonspecific background on the entire slide was a common problem. Similar results were obtained with plasmid libraries containing human DNA subcloned from the lambda phage libraries. In contrast, there was no background problem with the total chromosome library LA0XNL01, which contains a significantly smaller proportion of vector sequences in the probe mixture since the size of the human DNA inserts is much larger.

The suppression of repetitive sequences by this reannealing technique also permits the use of flow-sorted chromosome libraries to detect chromosomal domains within interphase nuclei. Typical examples of results obtained after hybridization of chromosome 1, chromosome 7 and chromosome 18 probe sets to normal human lymphocytes after acetic acid-methanol fixation are shown in FIGS. 5A–5F.

Discrete focal domains of hybridization signal are seen with all libraries that had scores of 2+ or more (see Table 2).

Most nuclei (n≧100 per estimate) exhibited two domains (60%–70%); however, a significant number showed only a single domain (20%–30%) or no hybridization signal at all (5%–10%). Accordingly, ca. 95% of male nuclei exhibited one and ca. 5% showed no hybridization signal when the X chromosome library DNA was used as probe. Notably, no nuclei with three domains were found with any of the chromosomal probe sets tested. In contrast, all metaphase spreads showed the decoration of both chromosome homologs without exception. This interphase variability may reflect, in part, the close juxtaposition of two individual domains in some cells, or the inability to resolve domains that actually occupy different areas within the nuclear volume but are unresolved when examined by two-dimensional imaging methods (see FIG. 5D; for discussion see also Cremer et al., *Exp. Cell Res.*, 176:199–220 (1988). The small number of nuclei exhibiting no hybridization signal may be a reflection of suboptimal hybridization conditions. It is of interest to note that the size of the intranuclear domains correlates reasonably well with the relative size of the cognate metaphase chromosome. These observations provide a definitive proof that the DNA of individual chromosomes exhibits a clear territorial organization in the interphase nucleus of a normal human cell.

Acetic acid-methanol fixed nuclear spreads, such as those shown in FIGS. 5A–5F, clearly retain the territorial organization for each of the chromosomes examined; however, the nuclear structure is not optimally preserved. Additional studies with specimens that possess better preservation of 3-D structure using paraformaldehyde fixed human diploid fibroblasts and a laser-scanning confocal fluorescence microscope assembly for 3-D image reconstruction have been done. The cells were fixed and permeabilized as described by Manuelidis and hybridized with chromosome library probes as outlined above. Manuelidis, L., *Ann. NY Acad. Sci.*, 450:205–221 (1985). The probe-competitor DNA mixture was applied directly to the slide and denatured at the same time as the cellular DNA. Results showed the arrangement of the chromosome 7 domains in the nucleus and the frequently observed helical structure of labeled chromatic within chromosome domains. The degree to which this helicity reflects true domain substructure or is an artifact reflecting preparation and fixation procedures is currently being investigated. Nevertheless, this preliminary observations establishes the feasibility of using chromosome specific probes to analyze the topography of chromosomal domains in the interphase cells.

EXAMPLE 2

Detection of Chromosome Aberrations in Tumor Cells by CISS Hybridization Using Chromosome-Specific Library Probes Cells TC 593 is a pseudotetraploid cell line (modal chromosome number, 83) established from a human glioblastoma; it grows in a flat, spreading fashion and contains many process. TC 620 is pseudotriploid with a modal chromosome number of 64 and was established from a human oligodendroglioma; it grows in an epithelial fashion. Both cell lines have been described in detail. Manuelidis, L. and E. E. Manuelidis, In: *Progress in Neuropathology*, Vol. 4, 235–266, Raven Press, N.Y. (1979). The present experiments made use of subclones C2B (TC 593) and C2B (TC 620) at approximately 180 passages after repeated subdloning from a single cell of the original tumor line cultured as previously described by Manuelidis and Manuelidis (see reference above). Standard hypotonic treatment and acid/methanol fixation of the cells were employed. Cremer et al., *Exp. Cell. Res.*, 176:199–220 (1988).

DNA Probes and Libraries

Phage DNA libraries from sorted human chromosomes were obtained from the American Type Culture Collection: LA01NS01 (chromosome 1), LL04NS01 (chromosome 4), LA07NS01 (chromosome 7), LL18NS01 (chromosome 18) and LA22NS03 (chromosome 22). Amplification of these libraries, isolation of human DNA inserts and biotinylation were carried out as described in Example 1. A probe specific for alphoid repeats on chromosome 7 (pa7t1) was the gift of H. Willard and specifically decorates pericentromeric heterochromatin of chromosome 7 under high stringency conditions (60% formamide). Waye et al., *Mol. Cell. Biol.*, 7:349–356 (1987); Cremer et al. *Exp. Cell. Res.*, 176:199–220 (1988). Some DNA probes were modified with aminoacetylfluorene (AAF); and detected as described by Cremer et al. for double labeling experiments. Landegent et al., *Exp. Cell Res.*, 153:61–72 (1984); Cremer, R. et al., *Exp. Cell Res.*, 176:199–220 (1988).

In Situ Hybridization and Detection of Hybridized Probes

CISS hybridization with biotinylated library DNA inserts and detection of hybrid molecules was generally carried out using standard conditions, as described in detail in Example 1. In double CISS hybridizations using biotinylated chromosome 7 library DNA inserts and the AAF-modified 7 alphoid probe, the latter probe was heat denatured separately and only added to the hybridization mixture at the end of the reannealing step at a final concentration of 10 µg/ml (see Example 1).

Digit Image Analysis-of Specifically Decorated Metaphase and Interphase Chromosome A VAX station II/GPX graphics workstation (Digital Equipment Corporation) with an ITEX FG 100-Q frame grabber (Imaging Technology) were used as previously described together with a Zeiss S-Planar 60 mm lens and a Dage-MTI 65 video camera. Manuelidis, L. and J. Borden, *Chromosoma*, 96:397–410 (1988). Images were digitized from negatives of metaphase spreads and interphase nuclei; the background was removed and polygonal regions were defined to specifically decorated metaphase chromosomes or interphase domains (see Example 1). A scan line algorithm was used to calculate histograms within the polygonal regions. Since the value of the histograms H(i) of a particular intensity (range 0–255) within the defined regions is the number of pixels at that intensity i, the area within the region falling within an intensity range $i_o$–$i_1$ is the integral of the histogram from $i_o$–$i_1$. Similarly, the 2-D integral in the region defined by the intensity range $i_o$–$i_1$ equals $\Sigma$ H(i).i.$i_o$ was chosen for each hybridization, in order to properly outline the decorated chromating and distinguish this area from background regions. $Di_1$ was set to the maximum value 255 in order to capture the entire intensity range above the threshold.

Measurements of total signal intensity versus area were designed as a control for the potential presence of variable chromosome domain extension within interphase nuclei. In interphase, a more extended chromosome domain might be expected to have a greater area (or volume) yet a lower fluorescence signal intensity per unit area. If a constant amount of hybridized DNA corresponds to a constant total fluorescence, the total signal intensity is a measure of labeled DNA content. It is also possible to measure 3-D hybridized volumes within nuclei and 3-D integrated total hybridized signals. Manuelidis, L. and J. Borden,

*Chromosoma*, 96:397–410 (1988). The background, b, was substracted from the discrete 2-D integral $\int\int I(x,y)dA$ within a labeled region R, to yield the total signal: $Sig_r = \int\int I(x,y)dA - b\int\int dA$, where dA is a single pixel. Similarily, the mean intensity within the region is calculated as 2-D integral/area or $\int\int I(x,y)dA / \int\int dA$.

The following is a description of the results, with reference to the appropriate figures, of the work described above. They clearly document structural and quantitative changes in the human glioma lines, including loss and gain of entire individual chromosomes and of chromosomal subregions. They also show that it has been possible to characterize both minor and predominant karyotypic features in each cell line. All chromosomes tested to date (i.e., 1, 4, 7, 18 and 22) clearly highlighted numerical and/or structural aberrations, some of which were subtle.

Detection of numerical and structural chromosome aberrations in metaphase spreads.

FIGS. 6A–6D, 7A–7J and 8A–8G and 12 show typical metaphase spreads from the malignant glioma cell lines TC 620 and 593 after CISS hybridization with biotinylated DNA inserts from each of the human chromosomes 1, 4, 7, 18 and 22. Hybridized inserts were detected with avidin fluorescein isothiocyanate conjugates (FITC) and cells were counterstained with 4,6-diamidino-2-phenylindole dihydrochloride (DAPI). Chromosomes designated as "complete" had an apparently normal size, centromere index and DAPI staining pattern. Despite this designation, these complete chromosomes may contain fine structural aberrations only detectable by additional investigations (see below). Apparently complete chromosomes 1, 4, 7, 18 and 22 were observed in both TC 620 and TC 593. Additionally, other homologs of these chromosomes showed significant rearrangements and abnormalities, including translocations and deletions. The predominant numerical and structural aberrations delineated in each of these cell lines are described below. A minimum of 25 good metaphase spreads were evaluated for each glioma line and for each chromosome. These data are summarized in FIG. 9.

Chromosome 1

Figure 9:
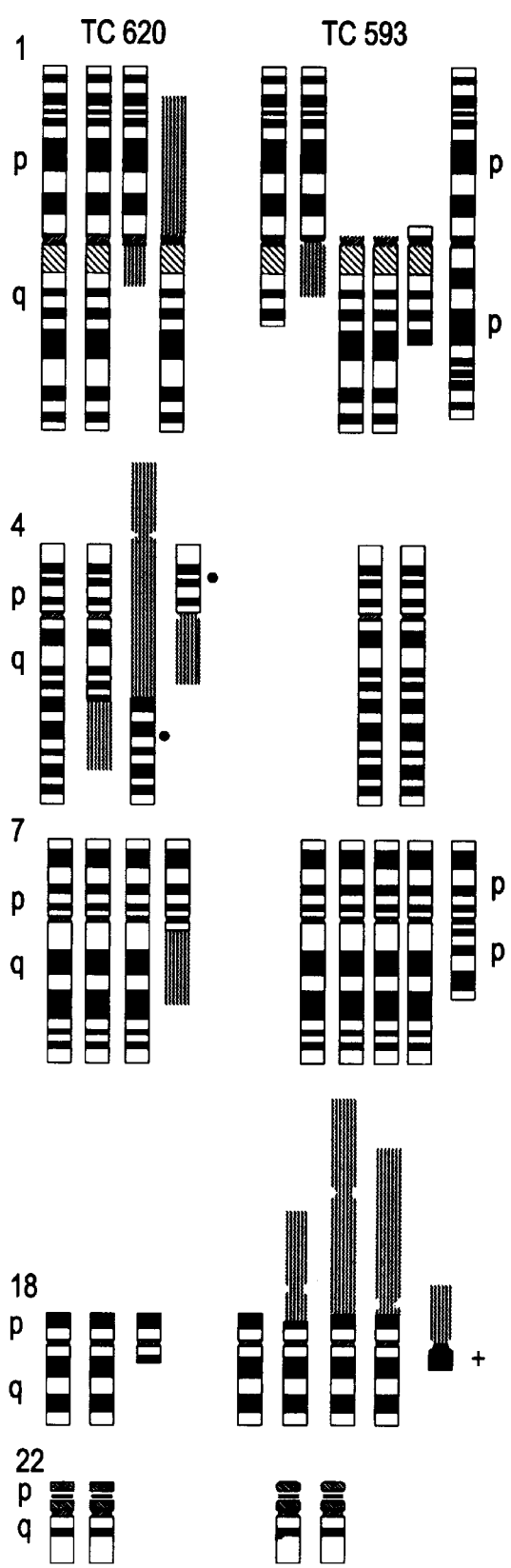
FIG. 9 is a summary chromosome idiogram of complete and aberrant chromosomes detected by CISS hybridization of library inserts of chromosome 1, 4, 7, 18 and 20 in glioma cell lines TC 620 (left) and TC 593 (right). G-bands (black) are shown with approximate breakpoints suggested by our data; the shaded areas with a wavy pattern are from other chromosomes that constitute part of the marker translocation chromosomes. The black dot beside two of the TC 620 translocated 4 segments indicates that the assignment of the chromosome 4 material is based on circumstantial evidence (e.g., size measurements). A small translocation of chromosome 18 material in ca. 20% of TC 593 metaphase spreads (+) also could not be further identified. Note the over-representation of 7p in both cell lines.

In TC 620, the oligodendroglioma line, chromosome 1 inserts decorated two apparently complete 1 chromosomes and two marker translocation chromosomes (FIGS. 6A, 6B, 9). One marker was metacentric and contained an entirely decorated 1q arm, but its p arm was from another chromosome (of unknown origin). The other marker chromosome was submetacentric and showed a small segment from another chromosome attached to the 1p arm. In both marker chromosomes breakpoints were localized close to the centromere in 1p11 or 1q11. The identification of the 1p segment was established by DAPI banding (FIG. 6B), by 5'-bromo-2'-deoxyuridine (BrdU) banding, and by hybridization with a 1p36.3 probe (data not shown); the 1p36.3 probe additionally revealed deletion of this subregion in one of the apparently complete 1 chromosomes. The overall picture was of a nearly trisomic representation of chromosome 1, with a common breakpoint, and subsequent translocation.

In TC 593, the glioblastoma line, an even more complex pattern of numerical and structural chromosome 1 aberrations was observed. In a sample of 50 metaphase spreads, the majority (52%) showed six aberrant chromosomes that were decorated; 14% of the metaphases showed five aberrant chromosomes, and 34% showed higher numbers of chromosomes 1 segments (up to 14). FIGS. 6C, D and 9 show the most typical, predominant karyotype and demonstrates the rapid definition of chromosome 1 abnormalities in this cell line. Aberrations included three acrocentric chromosomes with a consistent breakpoint in 1p1, chromosomes with a deletion of the distal park of 1q, a submetacentric translocation chromosome with a loss of the complete 1q, and an iso(1p) marker chromosome (see FIG. 9).

Chromosome 4

In TC 620, chromosome 4-specific inserts decorated one apparently complete chromosome 4, and three additional chromosomes with segments containing chromosomes 4 DNA (FIGS. 7F, 9). These latter segments on translocation chromosomes would have been difficult to rapidly and unambiguously define with banding procedures alone. The smallest of the translocated chromosome 4 segments formed part of an approximately metacentric chromosome. The two larger segments were found on submetacentric chromosomes of different overall size. In the smaller chromosome, the short arm and part of the long arm of 4 were present with an apparent breakpoint at 4q2, i.e., 4pter-4q2. In the larger submetacentric chromosome, a region that may represent the rest of 4 (4q2-qter) appears. Thus the predominant karyotype of TC 620 showed only slightly more than two equivalents of chromosomes 4 (see also the area measurements described below). The non-4 regions have not been further defined.

In TC 593, there were generally only two chromosomes decorated by chromosomes 4 DNA inserts, and both of these were compatible with normal 4 chromosomes. Approximately 30% of the metaphase spreads in TC 593 showed an additional submetacentric chromosome with chromosome 4 material (FIG. 7E). Thus, although both 4 chromosomes were apparently normal, there was a significant under-representation of this chromosome in this pseudotetraploid line (FIG. 9).

Chromosome 7

Three complete 7 chromosomes, and one smaller metacentric chromosome containing translocated 7 material were typically found in TC 620 metaphase spreads (FIGS. 8A, 9). The translocated chromosome 7 material included the short arm of chromosome 7 (as shown by DAPI banding; cf. FIG. 8B) and the pericentromeric heterochromatin with the breakpoint in 7q1 (see also below).

In TC 593, five chromosomes entirely decorated by chromosome 7 insert probes were regularly observed (FIGS. 7G, 8E). Four of these appeared to represent complete number 7 chromosomes, whereas one was smaller and metacentric. DAPI banding (FIG. 8E, insert) and size measurement (cf. FIG. 13) were consistent with an iso(7p). This conclusion was further supported by double in situ hybridization experiments with biotinylated chromosome 7 inserts (detected with avidin FITC) and chromosome 7-specific alphoid AAF labeled sequences (detected with tetramethylrhodamine isothiocyanate (TRITC) conjugated second antibodies). They showed that only the four complete 7 chromosomes, contained a detectable 7 centromeric signal (metaphase, FIGS. 7G, H; interphase, FIGS. 7I, J). Thus, the iso(7p) marker chromosome did not have a characteristic centromeric region as it lacked both the 7 alphoid sequences and a small block of heterochromatin at 7q11 (see FIG. 8E, insert). In contrast, all four 7 chromosomes of TC 620 were labeled with the 7 alphoid probe (data not shown).

Chromosome 18

In TC 620, two apparently complete 18 chromosomes and a truncated minute chromosome were entirely decorated (FIGS. 8C, D, 9). This truncated chromosome is 18q- (and possibly also 18p-). The rest of the chromosome 18 region(s) was never detected.

Three translocation chromosomes involving chromosome 18 material were typically detected, in addition to an apparently normal chromosome 18 in TC 593 metaphase spreads (FIGS. 8F, G, 9). In a minor proportion of metaphases there was a small additional translocation observed. The exact chromosomal region from which this translocated 18 material derived could not be resolved by DAPI staining. The predominant karyotype for 18 is therefore close to tetrasomic in this cell line, but is under-represented in the pseudotriploid TC 620.

Both the 18q-marker chromosome in TC 620 and the three translocated 18 chromosomes in TC 593 hybridized strongly to a chromosome 18-specific alphoid repeat. Accordingly, both intact and aberrant 18 chromosomes could also be counted after in situ hybridization with this centromeric probe. Cremer, T. et al., *Exp. Cell Res.*, 176:199–200 (1988) (see also below). DAPI banding and hybridization to 18-specific alphoid repeats indicated that these translocation chromosomes include the entire 18q region and the centromere, with breakpoints in 18p.

Chromosome 22

Figure 10A:
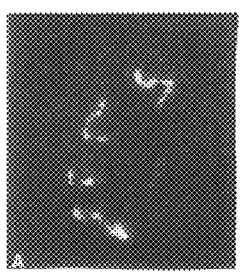
FIGS. 10A–10H show representative nuclei reflecting metaphase abnormalities in glioma cell lines (cf.
Figure 10B:
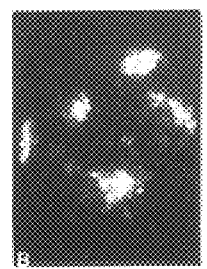
Figure 10C:
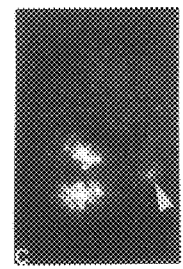
Figure 10D:
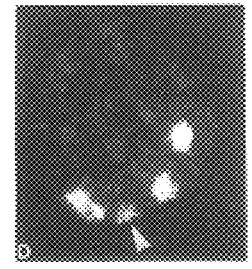
Figure 10E:
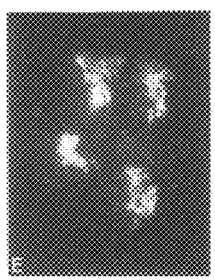

Two apparently normal 22 chromosomes were visualized in most TC 620 and TC 593 metaphase spreads (FIG. 10E). It was difficult to ascertain small translocations of this chromosome since hybridization with chromosome 22 inserts resulted in some cross-hybridization to other chromosomes. Some of this cross-hybridization is probably due to shared sequences from the nucleolus organizer regions (on five normal acrocentric human chromosomes) and to shared sequence motifs at the centromeres. McDermid, H. E. et al., *Chromosoma*, 94:228–234 (1986) and see Example 1. Finally, it should be noted that in constrast to conventional banding analysis, the current experimental approach clearly delineates numerical and structural chromosome aberrations in metaphase spreads of very poor quality (FIGS. 10G, H) or in early prophase nuclei (FIG. 10A). These preparations are not accessible to banding analysis, as the chromosomes extensively overlie each other.

Evaluation of Chromosome Domains in Interhase Nuclei

Figure 10F:
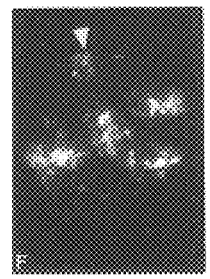
Figure 10G:
Figure 10H:
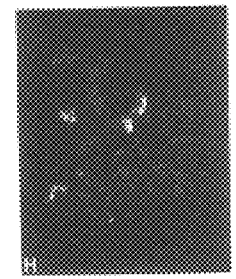

One potential advantage of in situ methods is that individual human chromosomes may be directly visualized as discrete territories in interphase nuclei and thus can be of value in the analysis of solid tumor speciment. Manuelidis, L., *Hum. Genet.*, 71:288–293 (1985); Schardin, M. et al., *Hum. Genet.*, 71:281–287 (1985); Pinkel, D. et al., *Proc. Natl. Acad. Sci. USA*, 83:2934–2938 (1986). This feature of nuclear topography, also apparent in the malignant cells examined here (FIGS. 7A–D, I, 10B–F), was evaluated for its accuracy and diagnostic usefulness. FIG. 10A shows three apparently complete 7 chromosomes and one translocated 7p arm in a prophase TC 620 nucleus. FIGS. 3A–3D, and 10B show five chromosome 7 domains in interphase nuclei of TC 593, as previously depicted in metaphase spreads. FIG. 10C shows a TC 620 interphase nucleus with two 18 domains of comparable sizes to those seen in normal diploid nuclei (see Example 1). A third, appreciably smaller, decorated 18 domain was also detected and represents the truncated 18 chromosomes seen in metaphase spreads described above. FIG. 10D shows four chromosome 18 domains in an interphase nucleus of TC 593, which again is comparable to the numbers in metaphase nuclei. FIG. 10E shows a TC 620 interphase nucleus with four chromosomes 1 domains, while FIG. 10F shows a TC 593 nucleus with at least five separate chromosome 1 domains (compare FIGS. 6A, B and C, D, respectively).

While the hybridization patterns of nuclei shown in FIGS. 10A–H were highly characteristic for each cell line, counts of interphase chromosome domains have some inherent difficulties. As an example, FIG. 11A (dark columns) presents an analysis of the counts of labeled interphase domains in randomly selected nuclei of diploid human lymphocytes hybridized with 7 library inserts. Although the number and relative size of chromosome specific domains can be accurately assessed in the majority of nuclei, not all nuclei present a reliable index of the chromosomal constitution, since a considerable fraction of nuclei reveal only one decorated domain and occasional nuclei show no signals. Furthermore all domains are not always cleared separable in these 2-D preparations.

FIGS. 11A–E show representative counts of these preparations. In agreement with TC 593 metaphase counts of chromosome 4, nuclear counts generally showed two clearly separated domains (FIG. 11E). However, the percentage of two-signal preparations was smaller in interphase than in metaphase (45.3% vs. 64%). This artifactual decrease was largely due to a corresponding increased percentage of nuclei showing only one decorated domain or no signal at all. Counts of zero or one domain were not present in metaphase spreads. Significantly, 19.3% of the interphase TC 593 nuclei displayed three clearly separated chromosome 4 domains, and these extra domains were not present in interphase nuclei of diploid human lymphocytes hybridized to this or other libraries under the same conditions (FIG. 10A; Example 1). Finally, the ratio of two versus three domains was identical for both metaphase and interphase cells. Thus interphase nuclei can be reliably used for the detection of extra copies of a single chromosome or chromosomal segment but have limited reliability for detecting the loss of chromosome copies.

In situ hybridization of probes from subregions of interphase chromosomes may more accurately reflect general counts of chromosomal constitution than library probes (FIG. 11A), provided they are done under appropriately high stringency conditions Rappold, G. et al., *Hum. Genet.*, 67:317–325 (1984); Cremer, T. et al., *Hum. Genet.*, 74:346–352 (1986); Cremer, T. et al., *Exp. Cell Res.*, 176:199–220 (1988). However, such regional segment probes do not delineate translocated elements or aberrant chromosomes that lack this segment. Therefore such probes are also not entirely accurate. For example, counts of chromosomes 1 in TC 620 and TC 593 with a probe specific for 1q12 indicated fewer 1 chromosomes than shown here with CISS hybridization (FIG. 9). Cremer, T. et al., *Exp. Cell Res.*, 176:199–220 (1988). Counts of chromosome 7 using only a centromeric sequence further emphasize this point (see above). Double in situ hybridization with the AAF-modified 7 alphoid probe and biotinylated chromosome 7 library inserts typically showed interphase nuclei with five domains, of which only four were simultaneously labeled by the centromeric probe (FIGS. 7I, J, 11C). In TC 620, however, both probes gave identical results (FIG. 11B).

Over Representation and Under Representation of Specific Chromosomes

The relative chromosomal dosage in these glioma lines, was also assessed with particular interest in chromosome 7, which has been noted to be generally over-represented in gliomas. Bigner, S. H. et al., *Cancer Genet. Cytogenet.* 29:165–170 (1986); Shapiro, J. R., *Semin. Oncol.*, 13:4–15 (1986). For comparison, other individual chromosome probes were used as controls. Metaphase chromosomes counts have shown that TC 620 is pseudotriploid with a modal number of 64 chromosomes, while TC 593 is pseudotetraploid with a modal number of 83. Manuelidis, L. and Manuelidis, E. E., IN: *Progess in Neuropathology*, Vol. 4, pp 235–266, Raven Press, N.Y. (1979). Accordingly, a chromosome and its segments together would be present in a balanced state if three complete copies were present in TC 620, and four in TC 593.

A relative over-representation is present if more than these respective copy numbers can be demonstrated. A number lower than the expected (trisomic or tetrasomic) value indicates that the chromosome is relatively under-represented in the karyotype. In cases where additional DAPI banding information was sufficient to define the selectively decorated abnormal chromosome, the chromosome pieces labeled by the chromosome-specific inserts were put together for analysis (FIG. 9). In the second approach, computer analyses were used to independently verify these results (see below).

TC 620 analyzed by banding showed the equivalent of three 1 chromosome and thus indicated a balanced state for this chromosome. The same was true for the 1p arm in TC 593 which was present in four copies. However, the distal part of 1q was under-represented in TC 593 (see the detailed description given above). In both glioma lines, 7q appeared to be balanced, while 7p was over-represented once in TC 620 and twice in TC 593. Additionally, in both glioma lines chromosomes 22 was clearly under-represented. In order to confirm this finding, double in situ hybridization with inserts of chromosomes 7 and 22 was performed. An example of this is shown in FIG. 12 and demonstrates over-representation of 7 DNA and under-representation of 22 DNA in the same cell. Metaphase counts done in both cell lines by this method of analysis are depicted for chromosome 7 in FIGS 11B, C (dark column) and for chromosome 22 in FIG. 11E. In summary, these two gliomas both show relative under-representation of chromosome 22 and over-representation of the 7p arm. The significant under-representation of chromosome 4 in TC 593, and a portion of 4 in TC 620 is also notable.

Digitized images were also used to quantitatively measure decorated areas in metaphase preparations and in interphase cells where chromosomal domains were well resolved. Quantitative evaluation of chromosome equivalents (Table 3) indicated highly concordant numbers for interphase versus metaphase in 5 of 6 examples; only in TC 593 decorated with 18 inserts was there a discrepancy. This may be due to the small sample size.

Table 3.

Twenty-four metaphase spreads showing the predominant number of chromosomes decorated with DNA inserts from libraries of chromosomes 4, 7 and 18 were compared to twenty-eight interphase nuclei with well-separated domains using the same probes. Images were taken under identical (linear film) conditions and digitized. In each metaphase spread, areas obtained for each normal and aberrant chromosome were divided by the mean area obtained for n apparently complete chromosomes. In interphase nuclei, domains were compared assuming that the largest n-labeled domains represented complete (normal) interphase chromosomes. Thus the sum of these normalized values represents a measure of the number of specific chromosomes equivalents in a single cell. The mean values of several cells are shown for each case. The mean numbers of chromosomes equivalents obtained for interphase and metaphase cells show a strong overall correlation coefficient of $r=+0.95$. Compared with area measurements, the mean numbers of chromosomes equivalents determined by 2-D intensity integrals (See above) showed an overall correlation coefficient of $r=+0.99$.

TABLE 3

Mean number of chromosome equivalents measured by digital image analysis in malignant glioma cell lines after CISS hybridization

| Chromosome | Cell Line | Chromosome equivalents | | |
|---|---|---|---|---|
| | | Interphase | Metaphase | Expected |
| 4 | TC593 | 2.0 | 2.0 | 4.0 |
| | TC620 | 2.5 | 2.4 | 3.0 |
| 7 | TC593 | 4.4 | 4.6 | 4.0 |
| | TC620 | 3.5 | 3.3 | 3.0 |
| 18 | TC593 | 3.0 | 3.6 | 4.0 |
| | TC620 | 2.5 | 2.3 | 3.0 |

Chromosome equivalents derived from digital image analysis independently confirm the relative repsentation of target chromosomes noted in both glioma lines by DAPI banding. The segments that comprise the total metaphase signal are further detailed graphically in FIG. 13. Computer analysis was especially useful in cases where the breakpoints involved in translocated segments could not be unambiguously defined. They were also of value in a quantitative assessment of interphase-metaphase correlations, and of normal and aberrant chromosomes with distinctly different sizes.

EXAMPLE 3

Rapid Detection of Human Chromosome 21 Aberrations by in Situ Hybridization

DNA Probes

All plasmids contain inserts of human chromosome 21 that were mapped to 21q22.3. Moisan, J. P., Mattei, M. G., Baeteman-Volkel, M. A., Mattei, J. F., Brown, A. M. C., Garnier, J. M., Jeltsch, J. M., Masiakowsky, P., Roberts, M. & Mandel, J. L. (1985) Cytogenet. Cell Genet. 40, 701–702 (abstr.). Tanzi, R., Watkins, P., Gibons, K., Faryniarz, A., Wallace, M., Hallewell, R., Conneally, P. M. & Gusella, J. (1985) Cytogenet. Cell Genet. 40, 760 (abstr.). Van Keuren, M. L., Watkins, P. C., Drabkin, H. A., Jabs, E. W., Gusella, J. F. & Patterson, D. (1986) Am. J. Hum. Genet. 38, 793–804. Nakai, H., Byers, M. G., Watkins, P. C., Watkins, P. A. & Shows, T. B. (1987) Cytogenet. Cell Genet. 46, 667 (abstr.). Munke, M., Foellmer, B., Watkins, P. C., Cowan, J. M., Carroll, A. J., Gusella, J. F. & Fracke, U. (1988) Am. J. Humm. Genet. 42, 542–549. All inserts were either known or verified by Southern blot analysis to be single-copy DNA: the plasmids other than pS2 are subclones derived from a λ phage library or a cosmid library. Van Keuren, M. L., Watkins, P. C., Drabkin, H. A., Jabs, E. W., Gusella, J. F. & Patterson, D. (1986) Am. J. Hum. Genet. 38, 793–804. Masiakowski, P., Breathnach, R., Bloch, J., Gannon, F., Krust, A. & Chambon, P. (1982) Nucleic Acids. Res. 10, 7895–7903. Watkins, P. C., Tanzi, R. E. Gibbons, K. T., Tricoli, J. V., Landes, G., Eddy, R., Shows, T. B. & Gusella, J. F. (1985) Nucleic Acids Res. 13, 6075–6088. Watkins, P. C. Watkins, P. A., Hoffman, N. & Stanislovitis, P. (1985) Cytogenet. Cell Genet. 40, 773–774 (abstr.). The plasmids are listed in Table 4 with the Human Gene Mapping Workshop symbols and the approximate insert fragment length. Kaplan, J. C. & Carrit, B. (1987) Cytogenet. Cell Genet. 46, 257–276.

TABLE 4

Plasmids with inserts from 21q22.3

| Plasmid | | Insert length kb | Plasmid | | Insert length kb |
|---|---|---|---|---|---|
| BCEI | pS2 (23) | 0.6 | D21s56 | pPW520-10R | 4.6 |
| D21S3 | pPW231F | 0.8 | | pPW520-11R | 1.8 |
| | pPW231G | 0.7 | D21S57 | pPW523-10B | 6.5 |
| D21S23 | pPW244D | 1.0 | | pPW523-1H | 7.0 |
| D21S53 | pPW512-6B | 3.0 | | pPW523-5R | 2.2 |
| | pPW512-8B | 3.8 | | pPW523-10R | 3.8 |
| | pPW512-1H | 2.9 | | pPW523-19R | 2.5 |
| | pPW512-16P | 2.7 | D21S64 | pPW551-8P | 1.9 |
| | pPW512-18P | 1.6 | | PPW551-12P | 4.2 |
| | pPW512-4R | 4.7 | D21571 | pPW519-10P | 0.8 |
| | pPW512-12R | 2.0 | | pPW519-11P | 3.0 |
| D21S55 | pPW518-4H | 1.6 | | pPW519-1R | 6.0 |
| | pPWS18-10P | 2.9 | | pPW519-8R | 2.9 |
| | pPW518-5R | 5.2 | | pPW519-9R | 1.7 |
| D21556 | pPW520-5B | 5.0 | | pPW519-14R | 4.0 |
| | pPW520-6B | 1.0 | | pPW519-22R | 1.8 |

Preparation of plasmid DNA was according to standard protocols. Maniatis, T., Fritsch, E. F. & Sambrook, J. (1982) Molecular Cloning: A Laboratory manual (Cold Spring Harbor Lab., Cold Spring Harbor, N.Y.). Various probe sets were obtained by pooling plasmids (equal molar amounts), resulting in DNA probe complexities of 95 kb (all plasmids listed). 75 kb (plasmids labeled with an asterisk), or 29 kb (plasmids labeled with a dagger).

The human chromosome 21 genomic library LL21NS02 was obtained from the American Type Culture Collection and amplified on agar plates as recommended. Phage DNA was prepared and digested wtih HindIII, and the DNA inserts were separated from the vector arms by preparative gel electrophoresis in 0.6% agarose. DNA was isolated from gel slices by electroelution; purified by Elutip-d chromatography. (Schleicher & Schuell); extracted with phenol/chloroform, 1:1 (vol/vol); and precipitated with ethanol.

Human Cells

Metaphase spreads and interphase nuclei were prepared from (i) lymphocyte cultures of normal (46, XY) individuals, (ii) lymphocytes of Down syndrome (47, +21) individuals, (iii) chroionic villi samples cultured for prenatal diagnosis (ii and iii were provided by T. Yan-Geng, Yale University Cytogenetics Laboratory), and (iv) cultures of TC620, an oligodendroglioma-derived pseudotriploid cell line. Manuelidis, L. & Manuelidis, E. E. (1979) in Progress in Neuropathology, ed. Zimmerman, H. M. (Raven, Press New York), Vol. 4, pp. 235–266. Standard techniques of colcemid treatment, hypotonic treatment, and methanol/acetic acid fixation were used. Biopsy material from the cortical region of a "normal" human brain (46, XX) was fixed, sectioned, and permeabilized as described. Manuelidis, L. & Borden, J., *Chromosoma*, 96:397–410 (1988).

In Situ Hybridization

Various comb in ations of plasmid DNA, labeled with Bioll-dUTe by nick-translation, were used for hybridization at concentrations ranging from 2 to 15 µg/ml depending on the pool size. Brigati, D. J., Myerson, D. Leary, J. J., Spalholz, B., Travis, S. Z. Fong, C. K. Y. Hsiung, G. D. & Ward, D. C. (1983) Virology 126,32–50. For example, 15 µg/ml was used when the probe mixture contained 94 kilobases (kb) of insert DNA; the probe concentration was decreased in proportion to the sequence complexity of the probe mixture. The size of the probe DNA was adjusted to a length of 150–250 nucleotides empirically by varying the DNase concentration in the nick-translation reaction. The hybridization cocktail also contained 50% formamide, 0.30 M NaCl, 0.03 M sodium citrate (pH7), 10% (wt/vol) dextran sulfate, and on occasion 0.5 mg of sonicated salmon sperm DNA per ml. Simultaneous denaturation of probe and target DNA was carried out at 75° C. for 6 min (metaphase spreads) or 94° C. for 11 min (tissue slices). Hybridization reactions were incubated at 37° C. overnight.

Delineation of individual chromosomes with DNA probes derived from sorted human chromosomes was done by (CISS) hybridization as described above. Briefly, biotinylated chromosome 21 library DNA inserts (5 µg/ml), DNase-digested human genomic DNA (200 µg/ml), and salmon sperm DNA (800 µg/ml) were combined in the hybridization solution, heat-denatured, and partially prehybridized for 10–30 min at 37° C. before application to a separately denatured specimen.

Posthybridization washes, detection of hybridized probe by using either alkaline phosphate-conjugated avidin or fluorescein isothiocyanate-conjugated avidin, and photographic conditions were as described in Example 1. When probe sets containing 29 kb or less of target sequence were used, the fluorescein isothiocyanate detection was generally enhanced by one cycle of signal amplification as described in Example 1.

All quantitative analyses of interphase signals were carried out by using slides from several independent experiments, with more than 100 nuclei being analyzed per slide. Comparison of signals in normal and trisomic samples was done in a blind-study fashion.

This work demonstrated that CISS hybridization, under the conditions described, resulted in rapid detection of numerical and structural aberrations of chromosome 21 in both metaphase and interphase cells.

Use of Cloned DNA Fragments From Human Chromosome 21 to Specifically Label Chromosomes in Lymphocyte Metaphase Spreads and Interphase Nuclei The maximal amount of unique sequence DNA in the probe set was ca94 kb; this probe set resulted in a clearly visible labeling of the terminal region of both chromatids of the chromosome 21 homologs (see FIG. 14B). These signals were seen unambiguously and without exception in all metaphase spreads, even in spreads of poor quality or from prophase cells (not shown). In normal interphase cells, the majority (65–75%) of nuclei exhibited two signals (see FIG. 14C), 25–30% showed one signal, and less than 5% showed no signal. Nuclei with three signals were found only rarely (<0.2%) and may reflect incomplete hybridization to a few tetraploid cells in the sample. Similar results were obtained with probe sets containing 29 or 75 kb of DNA. With probe sets containing fewer than 20 kb of insert DNA, there were increased numbers of cells with less than two signals. Thus, these probe sets were deemed unsuitable for diagnostic purposes. However, such probes still yielded specific signals on the majority of chromosomes 21, even with a 6-kb single-copy DNA (see FIG. 14A), especially when signal amplification was used.

Use of Chromosome Library DNA CISS Hybridization for Detecting Chromosome 21

Chromosome 21 was specifically and entirely decorated in normal lymphocyte metaphase spreads, although some additional minor binding sites were seen at or near the centromeric region of other acrocentric chromosomes, especially chromosome 13 (normal karyotype not shown; FIG. 14F). Suppression with additional DNA including a plasmid L1.26, which detects a repetitive DNA located predominantly at the centromeric region of chromosomes 13 and 21, did not efficiently suppress the minor non-21 chromosomal signals. Devilee, P., Cremer, T., Slagboom, P., Bakker, E., Schoil, H. P., Hager, H. D. Stevenson, A. F. G., Cornelisse, C. J. & Pearson, P. L. (1986) Cytogenet. Cell Genet. 41,193–201. Quantitative evaluation of interphase nuclei signals again showed a negligible portion of nuclei with three signals; however, a significant increase in nuclei with less than two signals was observed (50–60% with two signals, 35–45% with one signal, and 5–10% without a signal). The numerical differences observed with the two different probes can be explained in part by the number of nuclei (up to one of three) that were excluded from the latter analysis because they exhibited larger and more diffuse signals, most likely from more than one chromosome that could not be resolved unambiguously as two separate chromosome domains in a two-dimensional representation. The minor cross-hybridizing sites noted above presented a second experimental complication but did not adversely influence data interpretation.

Testing of Cells Containing Chromosome 21 Aberrations

The optimal (94 kb) plasmid pool as well as CISS hybridization with chromosome 21 library inserts were tested further by using cells containing chromosome 21 aberrations. Both probe sets permitted a fast and unambiguous diagnosis of trisomy 21 in all metaphase spreads from Down syndrome lymphocyte cultures (see examples in FIGS. 14D and E). Furthermore, the quantitative distribution of hybridization signals in interphase nuclei of the same preparation, analyzed as described above, was similar with either type of probe [<5% of cells with no signal, 5–15% with one signal, 25–35% with two signals, and 55–65% with three signals (FIGS. 14F–J)]. Although the library DNA inserts gave up to 15% of four-signal nuclei (compare FIGS. 14F and G), most likely due to the minor binding sites on other chromosomes, the plasmid pool revealed only a negligible percentage of nuclei (<0.2%) with four signals. These results indicate that trisomy 21 can be detected in a diagnostically meaningful way with small populations of non-mitotic cells.

Localization of Chromosome 21 DNA in Embryonic Chorionic Villi Cells

Embryonic chroionic villi (CV) cells were also investigated with the 94 kb plasmid probe sets in a case where the father had a reciprocal t(4:21) translocation. Hybridization to metaphase spreads of the CV cells showed that the translocated chromosome (4pter→4q33::21q11.2→21qter) was indeed inherited by the fetus (see FIGS. 13L and M). The signals in the interphase cell nuclei (see FIG. 14K) of the CV cells had a distribution that paralleled that of cells with a normal karyotype (see above), indicating a balanced representation of 21q22.3 and excluding Down syndrome as a possible diagnosis. A small increase of nuclei with three and four signals (both <5%) over that of normal lymphocytes was also observed, probably reflecting a higher portion of tetraploid cells in such CV samples.

Localization of Chromosome 21 DNA in of Glioma Tumor Cells

The diagnostic potential of the chromosome 21 probes was further tested by using a glioma tumor cell line, TC620, known to be pseudotriploid with a highly rearranged genome. Cremer, T. et al., *Exp. Cell Res.*, 176:199–220 (1988); Cremer, T. et al., *Hum. Genet.*, In Press, (1988); Manuelidis, L. and E. E. Manuelidis, In: *Progress in Neuropathology*, 4:235–266 (ed. Zimmerman, H. M.) (1979). The metaphase spreads revealed two apparently normal chromosomes 21 and one translocation chromosome (see FIGS. 14N and O). Interestingly, the chromosome 21 DNA on the translocation chromosome labeled by the library probe has a size equivalent to a normal 21q region, thus suggesting a Robertsonian translocation event. However, fine structural aberrations of 21q (i.e., small deletions, etc.) cannot be excluded by this analysis. The interphase signals seen with both the plasmid probe set and the library inserts were consistent with trisomy 21q22.3 and trisomy 21, respectively.

Localization of Chromosome 21 in DNA Sequences in Solid Tissues

The ability of the 94 kb plasmid probe set to localize chromosome 21 DNA sequences in solid tissues was also assessed. Both chromosomes 21 were clearly labeled by the probe, and located near the nucleolus; this nuclear location is consistent with the fact that chromosome 21 contains a ribosomal gene cluster that is usually localized in the nucleolus. This observation suggests that these probes may also prove useful for evaluating the frequency of chromosome 21 mosaicism in specific cell or tissue types. In addition, it should be of interest to see if the various karyotypic changes associated with the Down syndrome phenotype alter the normal nuclear topography of chromosome 21 in neuronal tissue.

EXAMPLE 4

Simultaneous Visualization of Seven Different DNA Probes by In Situ Hybridization Using Combinatorial Fluorescence and Digital Imaging Microscopy

MATERIALS AND METHODS

Human metaphase chromosomes were prepared by standard procedures. Prior to in situ hybridization, slides were washed in 1× phosphate-buffered saline (5 min; room temperature) and dehydrated through an ethanol series (70%, 90% and 100%; 5 min each). Slides were stored at −70° C. with Drierite powder.

DNA Probes

The following chromosome-specific a satellite DNA clones were used: pBS10.7AE0.6 (Baldini, unpublished), chromosome 3; p7tet (Waye, J. S. et al. (1987) *Mol. Cell. Biol.* 7:349–356), chromosome 7; pMR9A (Rocchi, M. et al. (1991) *Genomics* 9:517–523), chromosome 9; pBR12 (Baldini, A. et al. (1990) *Am. J. Hum. Genet.* 46:784–788), chromosome 12. pαH2 (chromosome 18) and pαH5 (chromosome 8) were cloned in our laboratory, while pRB2 (chromosome 11) was a gift of Dr. M. Rocchi (Bari, Italy). The chromosome specific plasmid libraries (Collins, C. et al. (1991) *Genomics*, 11:997–1006) were a gift of Dr. J. Gray (Livermore, Calif.). The following cosmid and phage clones were used: cptl, mapping to Xp2l (Ried, T. et al. (1990) *Hum. Genet.* 85:581–586); c-myc, mapping to 8q24 (Ried T. et al. (1992) *Genes Chromosom Cancer*, 4:69–74); c512, mapping to 21q22 (Lichter, P. et al. (1990) in *Molecular Genetics of Chromosome 21 and Down Syndrome*, ed. Patterson, D., Alan R. Liss, New York, N.Y., pp. 69–78); cosmid clone 26, mapping to 5q32 (unpublished data); cosSBl, mapping to 6p21 (Srivastava, R. et al. (1986) *Trans. Assoc. Am. Physicians*, Vol. XCIX); cosmid K40, mapping to 11p15 (Lichter, P. et al. (1990) *Science* 247:64–69). The cosmid clones specific for chromosome 5 (clones 26, 29, 56, 58, 92 and 121) were provided by Dr. Greg Landes (Integrated Genetics, Inc., Framingham, Mass.) and previously mapped b; Jennifer Lu (personal communication).

DNA was prepared according to standard techniques (Sambrook, J. et al. (1989) *Molecular cloning: a laboratory manual*, Cold Spring Harbor Lab., Cold Spring Harbor, N.Y.).

Probe Labeling

PCR's were performed using 10 ng of alphoid DNA clones or 100 ng of chromosome-specific libraries as template. Preferential amplification of insert DNA was achieved by using primers flanking the polylinker of each plasmid vector. T3 and T7 primers were used for the pBS vector, M13 forward and M13 reverse primers were used for pUC and pCR1000 vectors (all at a final concentration of 1 μM). PCR was carried out in 1.5 mM MgCl$_2$/10 mM Tris-HCl/50 mM KCl/0.001% gelatin/1.25 units of Tag polymerase (AmpliTaq; Perkin-Elmer/Cetus) in a total volume of 50 μl (10 μl when fluorescein-11-dUTP was used due to the limited amount of this reagent). The dNTP concentrations used in the PCR-labeling reactions are listed in Table 5. The highest concentration of modified nucleotides used was 75 μM. However, dinitrophenol (DNP)-11-dUTP at a concentration >37.5 μM strongly reduced the amplification efficiency (data not shown). When DNP-11-dUTP was used for combinatorial labeling, the concentrations were the same as for fluorescein-11-dUTP. The modified nucleotides were obtained from Boehringer Mannheim (digoxigenin (dig)-11-dUTP, fluorescein-11-dUTP), Sigma (Bio-11-dUTP) and Novagen (Madison, Wis.) (DNP-11-dUTP). The thermocycling was performed with a commercially available machine (Ericomp, San Diego). After an initial denaturation at 95° C. for 3 min, 32 cycles of PCR were carried out with denaturation at 94° C. for 1 min, annealing at 55° C. for 2 min and extension at 72° C. for 4 min (last cycle, 10 min). PCR products from the chromosome libraries were treated with DNase I to obtain an average fragment size of about 250 base pairs (bp) and were separated from free nucleotides by Sephadex G50 spin column. Cosmid and phage clones were labeled by standard nick-translation reactions. The final concentration of the modified nucleotides and the DNA clones used in these reactions were as follows: Bio, 50 μM (cosSB2, clone 58); dig, 40 μM (K40, clone 121); DNP, 40 μM (c512, clone 92); Bio/dig, 20 μM/30 μM (cptl, clone 56); Bio/DNP, 20 μM/30 μM (c-myc, clone 29) and dig/DNP, 20 μM/30 μM (clones 28 and 26).

TABLE 5

Labelling of Seven Centromere Probes

| | dNTP, μM | | | | | | |
|---|---|---|---|---|---|---|---|
| | AE.06 | p7tet | pBR12 | pMR9A | pRB2 | paH2 | paH5 |
| Bio-11-dUTP | 75 | | | 37.5 | 37.5 | | 25 |
| dig-11-dUTP | | 75 | | 37.5 | | 37.5 | 25 |
| FITC-11-dUTP | | | 75 | | 37.5 | 37.5 | 25 |
| TTP | 225 | 225 | 225 | 225 | 225 | 225 | 225 |
| dA, dC, dGTP | 300 | 300 | 300 | 300 | 300 | 300 | 300 |

FITC, fluorescein isothiocyanate

In Situ Hybridization and Detection
Centromeric repeats

After PCR amplification, the probes were used without further purification. The DNA solution was diluted 1:5 in 10 mM Tris-HCl/1 mM EDTA. One microliter of each probe was precipitated with 5 μg of salmon sperm DNA and 5 μg of yeast RNA and resuspended in 10 μl of 60% formamide, 2× standard saline citrate (SSC) and 5% dextran sulfate. Probe DNA was denatured at 75° C., 5 min, and immediately applied to the denatured chromosome specimens; a coverslip was added and sealed with rubber cement. The slides were denatured separately in 70% formamide/2× SSC for 2 min at 80° C. and dehydrated in an ethanol series. After overnight incubation at 37° C., the coverslips were removed and the slides were washed at 45° C. in 50% formamide/2× SSC three times, followed by three washes at 60° C. in 0.1×SSC. After a blocking step (in 4×SSC/3% bovine serum albumin for 30 min at 37° C.), the biotinylated probes were detected using streptavidin conjugated to the infrared dye Ultralite 680 (Ultra Diagnostic Corporation, Seattle, Wash.; final concentration, 2 μg/ml); the dig-labeled probes were detected with a rhodamine-labeled anti-dig IgG (Boehringer Mannheim). The fluorescein-1-dUTP (Boehringer Mannheim) labeled probes did not require any immunological detection step. 4',6-Diamidino-2-phenylimdole (DAPI) was used as a chromosome counterstain.

Chromosome painting

The amplification products were treated with DNase I to an average size of 150–500 bp. Five microliters of the amplification reaction mixture (50 μl) was precipitated with 5 μg salmon sperm DNA and 5 μg of yeast RNA, together with 10 μg total human competitor DNA, and then resuspended in 10 μl 50% formamide/2× SSC/10% dextran sulfate. The probe was denatured as described above and allowed to preanneal for 1 h at 37*C. Slides were denatured as described for the centromeric repeats. Hybridization took place overnight at 37° C. Slides were washed at 42° C. in 50% formamide followed by three washes at 60° C. in 0.5× SSC. The biotinylated sequences were detected with streptavidin conjugated to the infrared dye Ultralite 680; the dig-labeled sequences were detected with rhodamine-labeled anti-dig IgG (Boehringer Mannheim). DNP-labeled probes were detected with a monoclonal rat anti-DNP antibody (Novagen) and a secondary goat anti-rat antibody, conjugated to Fluorescein isothiocyanate (Sigma). DAPI was used as a DNA counterstain.

Cosmid clones

Eighty ng of each cosmid or phage was precipitated with 20 μg human competitor DNA and 5 μg each of yeast RNA and salmon sperm DNA. The detection of the differently labeled probe DNAs was performed as described above for the chromosome specific libraries.

Digital Imaging

Images were obtained using a Zeiss Axioskop epifluorescence microscope coupled to a cooled charge coupled device (CCD) camera (Photometrics, Tuscon, Ariz., PM512). Camera control and digital image acquisition (8-bit gray scale) employed an Apple Macintosh IIx computer. Fluorophores were selectively imaged using filter cubes specially prepared by Zeiss (Filter 487910 for fluorescein, filter 487915 for rhodamine and filter 487901 for DAPI) to minimize image offsets. The infrared filter (excitation 620–658 nm; dichroic, 650 nm, bandpass, 670–680 nm) is not a precision filter. Images taken using the latter filter were therefore slightly shifted. These were digitally realigned with the probe signals as reference.

Each set of three gray scale fluorescence images revealed probe signals that appeared in only one, in two, or in all three of the images (i.e., the seven combinatorial possibilities). Since the probe-positive regions were visually distinct and were relatively few in number, their combinatorial participation was readily identifiable by visual inspection of the image groups. As a step toward uniquely pseudocoloring these data regions on a combinatorial basis, the regions were isolated and segregated into seven separate (but still spatially aligned) gray scale subimages by using interactive graphics software. Data regions were blended (intensity was averaged) in those cases in which probe signals appeared in more than one of the original images.

The visual identification and manual interactive segregation of data regions was necessary due to limitations of currently available graphics software.

The seven intermediate gray scale images were then separately pseudocolored, a process that converts a gray scale to a tint scale. The pseudocolored images were then recombined through a simulated overlay. The multicolored composite image was simultaneously merged with a DAPI counterstain image (also pseudocolored) using software developed in our laboratory that combines images by picking maximum signal intensity at each pixel position. The digital imaging technique described above can be implemented on a general purpose computer, e.g., an Apple Macintosh IIx, using known image processing tools, as particularly arranged and operated in accord with the above methodology. A preferred such implementation, termed Gene Join, can be obtained from the Office of Cooperative Research, Yale University, Suite 401, 246 Church St., New Haven, Conn. 06510.

Photographs were taken with a Agfa matrix procolor slide printer using Kodak 100 HC color slide film.

RESULTS

Combinatorial Labeling of Probes by PCR

Chromosome-specific centromeric repeats and chromosome specific DNA libraries are frequently used as probes for fluorescence in situ hybridization (FISH) because of their utility in revealing chromosome aneuploidy or aberrations in interphase cells and tissues as well as the identification of marker chromosomes unrecognizable by conventional banding methods (Tkachuk, D. C. et al. (1991) *GATA* 8:67–74; Lichter, P. et al. (1991) *GATA* 8:24–35). Since clones containing such sequences generally have relatively small inserts, ranging in size from a few hundred nucleotides to a few kilobase pairs, we first chose to assess vector PCR as a general method for the combinatorial labeling of such clones. Bio, dig, DNP and fluorescein, all conjugated to dUTP, could be efficiently incorporated during the amplification reaction, alone or in combination, resulting in selective enrichment of labeled chromosome-specific sequences. Several combinations of nucleotide analogs were tested in order to establish the appropriate concentrations necessary to give an approximately equimolar mixture of each reporter in the probe. These nucleotide concentrations are listed in Table 5 and Table 6. Alphoid DNA clones specific for chromosomes 3, 7, 8, 9, 11, 12 and 18 and chromosome-specific libraries for chromosome 1, 2, 4, 8, 14 and X were then labeled combinatorially by vector PCR. Each combination with Bio, dig and DNP (or fluorescein-dUTP) singularly tested by in situ hybridization and each combination gave comparable signal intensities (data not shown).

Simultaneous Detection of Seven Centromere Repeat Probes

Figures 15A, 15B, 15C:
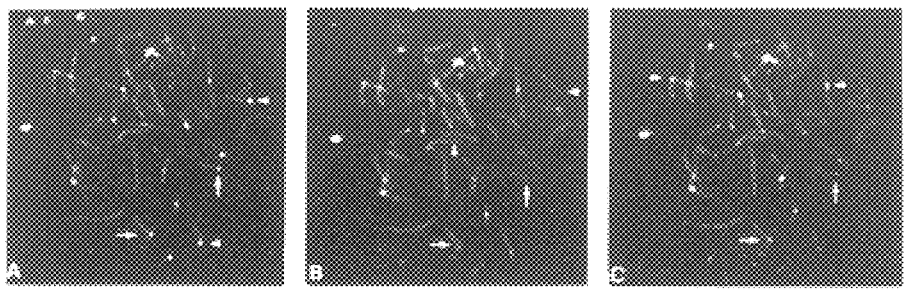
Figures 15D, 15E:
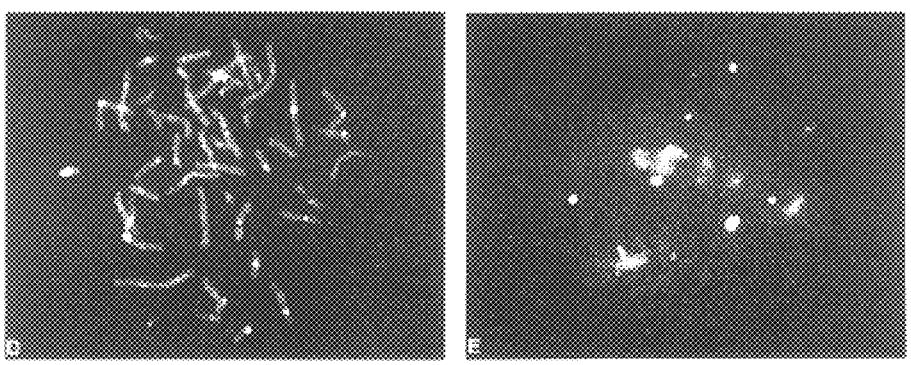

The chromosome-specific alphoid DNA clones and the modified nucleotide, used to label them are given in Table 5. The biotinylated probes were detected with an infrared fluorophore emitting at 680 nm (Ultralite 680) conjugated to streptavidin. The dig-labeled probes were detected with anti-dig antibodies coupled to rhodamine (630 nm emission) while the probes labeled with fluorescein-11-dUTP (580 nm emission) were detected directly. A separate gray scale image of each fluorophore was then acquired by using the CCD camera system. As shown in FIGS. 15(A–C), four pairs of chromosome-specific hybridization signals are seen in each image, as expected from the experimental design. Each of the source gray scale images have been pseudocolored to highlight the hybridization signals. One pair of signals appears uniquely on each of the images (see arrowheads), reflecting those probes that were labeled with only a single reporter. Two other signal pairs appear on two images each, while the third appears on all three images (see arrows). Thus each probe could be selectively identified by the fluorophore image combination on which the hybridization signal was detected. The gray scale signal regions from the images were segregated, pseudocolored and merged with computer software as described. FIG. 15D shows this merged image. Each of the seven centromere probes are seen as distinct colors on the DAPI (blue) counterstained metaphase chromosomes. The probes could also be clearly distinguished after hybridization to fixed human lymphocyte nuclei. FIG. 15E shows a merged image of an interphase nucleus hybridized with a mixture of the seven centromere probes.

Simultaneous Painting of Six Chromosomes. Detection of a Chromosomal Translocation Chromosome painting is a powerful and general approach to study chromosomal abnormalities. Here the probes are a complex composite of sequences cloned in plasmid or phage vectors with flow-sorted chromosomes used as the starting DNA source (Pinkel, D. et al. (1988) *Proc. Natl. Acad. Sci. USA* 85:9139–9142; Cremer, T. et al. (1988) *Hum. Genet.* 80:235–246). To demonstrate that combinatorial labeling also could be used for whole chromosome analysis, the libraries for chromosomes 1, 2 and 4 were singly labeled with Bio, dig and DNP, while the libraries for chromosomes 8, 14 and X were labeled combinatorially (see Table 6). Each probe set decorated a single chromosome pair when analyzed by FISH, with signal intensities on each fluorophore channel being of similar intensity (data not shown). The merged image (FIG. 15F) highlights the six target chromosomes in different pseudocolors while the remaining chromosomes exhibit the blue DAPI counterstain.

TABLE 6

Labelling of Chromosome-Specific Libraries

| | dNTP, μM | | | | | |
|---|---|---|---|---|---|---|
| | pBS2 | pBS14 | pBS1 | pBS4 | pBSX | pBS8 |
| Bio-11-dUTP | 75 | | | 37.5 | 37.5 | |
| dig-11-dUTP | | 75 | | 37.5 | | 37.5 |
| DNP-11-dUTP | | | 37.5 | | 37.5 | 37.5 |
| TTP | 225 | 225 | 262.5 | 225 | 225 | 225 |
| dA, dC, dGTP | 300 | 300 | 300 | 300 | 300 | 300 |

Figures 15F, 15G:
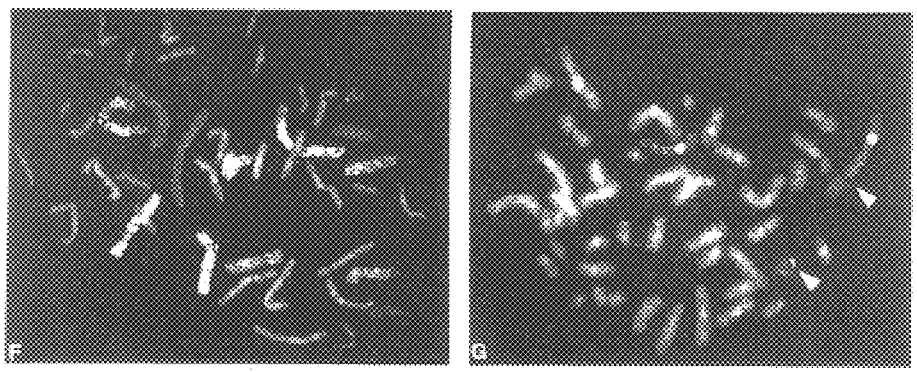
Figures 15H, 15I, 15J:

The PCR-generated libraries can also be used for detection of chromosomal translocations as exemplified in FIG. 15G. Metaphase spreads were obtained from lymphocytes of a healthy female donor whose karyotype (Giemsa banding) was shown to be 46, XX, t(2;14)(q37; q22). The metaphase spreads were investigated in order to clarify the origin of an identical translocation detected in the fetus of the donor. Using PCR-generated libraries for chromosome 2 (Bio) and chromosome 14 (dig), the reciprocal character of the translocation could be clearly demonstrated (see arrowheads).

Combinatorial Labeling and Gene Mapping

The feasibility of mapping multiple genes simultaneously by using the combinatorial labeling paradigm is demonstrated by the data presented in FIGS. 15(H–J). Six different cosmid and phage clones, previously mapped to chromosomes 5, 6, 8, 11, 21 and X in independent experiments, were cohybridized and separate gray scale fluorescence images collected and processed as described above. The merged image on a DAPI-counterstained metaphase spread is shown in FIG. 15H. The chromosomal location of each clone, as measured by both fractional length measurements (Lichter, P. et al. (1990) *Science* 247:64–69) and Alu-PCR hybridization banding (Baldini, A. and Ward, D.C. (1991)

Genomics 9:770–774), was identical to that obtained before (data not shown). Six cosmid clones with known locations on chromosome 5 were also hybridized simultaneously. FIG. 1I shows the distribution of these clones on both chromosome 5 homologs in a metaphase spread while FIG. 15J demonstrates that the relative order of the clones (i.e., the pattern of colors) is maintained in the interphase nuclei of a T lymphocyte. It should be noted that many of the signals appear as doublets, reflecting the fact that these sequences have already undergone DNA replication in this nucleus. Conversion of a probe signal from a singlet to a doublet can be used to monitor the replication timing of DNA segments during S phase.

DISCUSSION

A procedure that permits the analysis of up to seven probes simultaneously. Combinatorially labeled probes can be produced rapidly and reproducibly by either nick-translation or PCR amplification. However, the latter approach is particularly attractive for labeling clones with relatively small inserts (about 6 kilobases or less) since vector-derived PCR primers permit selective amplification of insert DNA sequences with high efficiency. For example, with the alphoid DNA clones, a typical 50 μl amplification reaction mixture yields sufficient labeled probe for about 250 in situ hybridizations. Not surprisingly, the yield for the chromosome library clone pool is lower; nevertheless, 100 ng of template gave enough amplification products to hybridize 10 slides. Reamplification of the primary PCR product pool could also be done without any detectable loss of probe complexity (data not shown). In contrast, using nick-translated plasmid libraries, 200 ng of DNA was required per slide. The negligible amount of labeled vector sequences in the PCR products also reduces the potential for vector sequence cross hybridization, a problem which was described by Nederlof et al. (1990) Cytometry 10:20–27.

The digital imaging capabilities of the cooled CCD camera and the computer software for pseudocoloring and merging signals from combinatorially labeled probes will play an important role in extending the number of simultaneously detectable probes beyond the seven reported here. The CCD camera is sensitive to light over a broad spectrum range. Infrared dyes, such as Ultralite 680, which are not visible by eye, can be imaged quite readily by the CCD camera. A series of fluorophores emitting in the 650 to 900 nm range, have recently been reported (Ernst, L. A. et al. (1989) Cytometry 10:3–10); this should increase the number of different fluorophores that can be used combinatorially for probe identification. Furthermore, the infrared dyes, such as Ultralite 680, offer certain advantages over the blue fluorophores, AMCA or Cascade Blue: i) sample autofluorescence is minimal at the longer wavelength, ii) DAPI counterstaining of metaphase chromosomes and interphase nuclei is possible (the emission of DAPI, AMCA and Cascade Blue overlap) and iii) the observed bleed-through of rhodamine signals with the DAPI filter when imaging AMCA fluorescence is more severe than the bleed-through of rhodamine signals using the infrared filter.

Digital imaging of combinatorially labeled probes also circumvents a universally thorny problem in multicolor analysis, that of precise image registration. When filter cubes are moved to collect the fluorescence emission of a single fluorophore, optical imperfections or mechanical motion may cause image displacement relative to each other; these registration offsets can be as large as 1 μm. This is extremely problematic when spatial relationships between signals are critical, such as in gene mapping. However, when multiple probes, combinatorially labeled, are cohybridized, signals from these probes appear on two or more of the separate fluorophore images, thus providing internal reference points for image registration. Provided that one hybridization signal set is directly tied to the complete image of a metaphase spread or interphase nucleus, i.e., by using a dual bandpass filter (Johnson, C. V. et al. (1991) GATA 8:75), all images can be aligned, irrespective of the number of separate images to be merged. Fluorescence in situ hybridization is becoming an increasingly powerful experimental tool, both for basic research and for clinical applications. The ability to visualize multiple probes simultaneously should streamline the screening of specimens for chromosomal aneuploidies and/or chromosomal rearrangements. This is of particular importance in cases where clinical samples are limited in number. In addition, by incorporating one or more appropriate reference clones (e.g., centromere repeats or unique sequence genes) in the experimental protocol, the assessment of gene dosage (loss of heterozygosity, aneuploidy and mosaics) or defining boundaries of chromosomal deletions should be more definitive and require less statistical analysis. The generation of physical mapping data, using either metaphase or interphase mapping strategies should be facilitated with combinatorial fluorescence as would studies focused on understanding the intranuclear topography of genes and chromosomes. It should be stressed that the assessment of the chromosomal map positions of several combinatorially labeled clones does not necessarily require the pseudocoloring and merging procedures. Displaying the signals separately as gray scale images, as shown in FIGS. 15(A–C), allows the physical ordering of probes, since combinatorially labeled clones appear in several gray scale images and can thus be identified. Manual segregation of the images is time-consuming, which in its present format reduces the rate at which clones can be mapped. This limitation can be eliminated by software to automate this step.

The use of commercially available nucleotide analogs conjugated to fluorescein is of particular value for clinical applications since it circumvents time-consuming and sometime troublesome immunological steps required to visualize haptenized probes. In addition, this results in an improved signal/noise ratio, which could enhance overall detection sensitivity, especially if a cooled CCD camera were used for imaging. It can be expected that other nucleotides with additional conjugated fluorophores will be available soon, which would both simplify and expand the combinatorial labeling strategy for multicolor hybridization assays even more.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:
1. A method of in situ hybridization to simultaneously detect multiple target sequences of interest in chromosomal DNA of interphase cells of nuclei thereof, the method comprising:
 (a) treating a sample of interphase cells or nuclei thereof to render chromosomal DNA present therein available for hybridization to sequences complementary thereto,
 (b) contacting said sample with a pool of DNA, wherein said pool comprises:
  i) different labeled DNA probes, each DNA probe comprising either DNA fragments labeled with a single fluorophores or a mixture of DNA fragments separately labeled with different fluorophores, such that each DNA probe generates an optically distinguishable signal, and each probe being specific for one human chromosome, of region thereof, suspected to be present in said sample; and ii) competitor DNA fragment, wherein said fragments comprise repetitive sequeneces complementary to sequeneces present in said sample and to sequeneces present in said probes, under conditions that allow hybridization of said competitor DNA fragments to said complementary repetitive sequeneces present in said sample and present in said probes sufficient to suppress cross-hybridization between said repetitive sequeneces in said probes amd in said sample and allow hybridization of said probes to specific target chromosomal sequeneces present in said sample, and c) detecting multiple hybridization signals simultaneously, wherein each detected signals is distinguishable and identifies a specific target chromosomal sequenece present in said sample.

2. The method of claim 1, wherein the labeled DNA probes and the competitor DNA fragments are combined before contacting with the sample of interphase cells or nuclei thereof.

3. The method of claim 2, wherein the labeled DNA probes are combined under conditions which allow the repetitive sequeneces in the competitor DNA fragments and repetitive sequences in the labeled DNA probes to preanneal and to thereby suppress cross-hybridizing repetitive sequences sufficiently to produce labeled DNA probes hybridizable specifically to the target sequences in chromosomal DNA.

4. The method of claim 1, wherein the sample of interphase cells or nuclei thereof are tumor cells, or nuclei thereof.

5. The method of claim 1, wherein the sample of interphase cells or nuclei thereof comprise uncultured cells from amniotic fluid or nuclei thereof.

6. The method of claim 1, wherein one of said target sequences is an individual chromosome or a region thereof.

7. The method of claim 6, wherein the labeled DNA probes are obtained from a library of DNA target chromosomes.

8. The method of claim 1, wherein the competitor DNA fragments are total human genomic DNA.

9. The methods of claim 1, wherein a carrier DNA is added to the pool of DNA.

10. The method of claim 1, wherein the labeled DNA probes and the competitor DNA fragments are DNA fragments smaller than 500 nucleotides.

11. A method of DNA hybridization for detecting target chromosomal DNA in situ in interphase cells of nuclei thereof, comprising:

a) providing labeled DNA probes having sequences which specifically hybridize to target chromosomal DNA, but have repetitive sequences which cross-hybridize to non-target chromosomal DNA, and competitor DNA fragments which contain the repetitive sequences, wherein the labeled DNA probes and the competitor DNA fragments are DNA fragments which range from 150–250 nucleotides in length:

b) combining i) the labeled DNA probes;

ii) competitor DNA fragments; and iii) a sample of interphase cells, or nuclei thereof, treated to render chromosomal DNA therein available for hybridization with the labeled DNA probes, under hybridization conditions wherein cross-hybridization between repetitive sequences in th DNA probes and the sample are sufficiently suppressed to allow the DNA probes to hybridize specifically to the target chromosomal DNA; and c) detecting the labeled DNA probes in order to detect the target chromosomal DNA in situ in interphase cells or nuclei thereof.

12. A method of DNA hybridization for detecting target chromosomal DNA is situ, comprising:

a) providing labeled DNA probes having sequences which specifically hybridize to target chromosomal DNA, but having repetitive sequences which cross-hybridize to non-target chromosomal DNA, and competitor DNA fragments containing the repetitive sequences;

b) combining i) the label DNA probes at a concentration equivalent to 5 to 30 micrograms per milliliter of a genomic DNA library of and individual human chromosome;

ii) the competitor DNA fragments at a concentration equivalent to about 100 to 200 micrograms per milliliter of total human genomic DNA; and iii) a sample of cells treated to render chromosomal DNA therein available for hybridization with the labeled DNA probes, under hybridization conditions wherein cross-hybridization between reptitive sequences in the DNA probes and the sample is sufficiently suppressed to allow the DNA probes to hybridize soecifically to the target chromosomal DNA; and c) detecting the labeled DNA probes in order to detect the target chromosomal chromosomal DNA in situ.

13. The method of claim 12, wherein the labeled DNA probes and the competitor DNA fragments are combined before combination with the sample of cells.

14. The methods of claim 13, wherein the labeled DNA probes and the competitor DNA fragments are combined under conditions which allow the repetitive sequences in the competitor DNA fragments and repetitive sequences in the labeled DNA probes to preanneal and to thereby suppress cross-hybridizing repetitive sequences sufficiently to produce labeled DNA probes hybridizable specifically to the target chromosomal DNA.

15. The method of claim 12, wherein the sample of cells are tumor cells.

16. The method of claim 12, wherein the sample of cells comprise uncultured cells from amniotic fluid.

17. The method of claim 12, wherein the target chromosomal DNA is an individual chromosome or a region thereof.

18. The method of claim 17, wherein the labeled DNA probes are DNA obtained from a library of DNA of the target chromosome.

19. The method of claim 12, wherein the labeled DNA probes and the competitor DNA fragments are DNA fragments ranging from 150–250 nucleotides in length.

20. The method of claim 12, wherein the competitor DNA fragments for the suppression of repetitive sequences are total human genome DNA.

21. The method of claim 12, wherein a carrier DNA is added to the combination of labeled DNA probes, competitor DNA fragments and the sample preparation.

22. The method of claim 12, wherein the labeled DNA probes are labeled with biotin.

23. The method of claim 12, wherein the cells are interphase cells, or nuclei thereof.

24. A method of DNA hybridization for detecting target chromosomal DNA in situ, comprising:
   a) providing labeled DNA probes having sequences which specifically hybridize to target chromosomal DNA, but having repetitive sequences which cross-hybridize to non-target chromosomal DNA, and competitor DNA fragments which contain the repetitive sequences;
   b) combining
      i) the labeled DNA probes;
      ii) the competitor DNA fragments; and
      iii) a sample of cells treated to render chromosomal DNA therein available for hybridization with the labeled DNA probes,
         under hybridization conditions wherein cross-hybridization between repetitive sequences in the DNA probes and the sample is sufficiently suppressed to allow the DNA probes to hybridize specifically to the target chromosomal DNA, wherein the concentrations of the labeled DNA probes and the competitor DNA fragments are selected such that the signal-to-noise confidence ratio interval (99%) for hybridization is at least 7.18±0.37 calculated using Fieller's theorem; and
   c) detecting the labeled DNA probes in order to detect the target chromosomal DNA in situ.

25. The method of claim 24, wherein the concentrations of the labeled DNA probes and the competitor DNA fragments are selected such that the signal-to-noise confidence ratio interval (99%) for hybridization is at least 8.11±0.35 calculated using Fieller's theorem.

26. The method of claim 24, wherein the cells are interphase cells, or nuclei thereof.

27. A method of in situ hybridization for distinguishably labeling individual human chromosomes, or regions thereof, in interphase cells of nuclei thereof comprising:
   (a) treating a sample of interphase cells or nuclei thereof to render chromosomal DNA present therein available for hybridization to complementary sequences,
   (b) contacting said sample with a pool of DNA, wherein said pool comprises:
      i) different labeled DNA probes, each DNA probe comprising either DNA fragments labeled with a single fluorophore or a mixture of DNA fragments separately labeled with different fluorophores, such that each DNA probe generates an optically distinguishable signal, and each probe being specific for one of said human chromosomes, of region thereof, suspected to be present in said sample; and
      ii) competitor DNA fragments, wherein said fragments comprise repetitive sequences complementary to sequences present in said sample and to sequences present in said probes,
         under conditions that allow hybridization of said competitor DNA fragments to said complementary repetitive sequences present in said sample and present in said probes, sufficient to suppress cross-hybridization between said repetitive sequences in said probes and in said sample, allowing hybridization of said probes to specific target chromosomal sequences present in said sample, to thereby distinguishable label individual human chromosomes, or regions thereof, in interphase cells of nuclei thereof.

28. A method of in situ hybridization for simultaneously visualizing individual human chromosomes, or regions thereof, in interphase cells or nuclei thereof comprising:
   (a) treating a sample of interphase cells or nuclei thereof to render chromosomal DNA present therein available for hybridization to complementary sequences,
   (b) contacting said sample with a pool of DNA, wherein said pool comprises:
      i) different labeled DNA probes, each DNA probe comprising either DNA fragments labeled with a single fluorophore or a mixture of DNA fragments separately labeled with different fluorophores, such that each DNA probe generates an optically distinguishable signal, and each probe being specific for one of said human chromosomes, or region thereof, suspected to be present in said sample; and
      ii) competitor DNA fragments, wherein said fragments comprise repetitive sequences complementary to sequences present in said sample and to sequences present in said probes,
         under conditions that allow hybridization of said competitor DNA fragments to said complementary repetitive sequences present in said sample and present in said probes, sufficient to suppress cross-hybridization between said repetitive sequences in said probes and in said sample and allow hybridization of said probes to specific target chromosomal sequences present in said sample; and
   c) detecting the optically distinguishable signals generated by DNA probes to simultaneously visualize each human chromosome, or regions thereof, in interphase cells or nuclei thereof.

29. A method according to claim 28, wherein the detecting step comprises:
   a) generating one or more digital images of the hybridized chromosomal DNA; and
   b) visually emphasizing those portions of the digital images which represent optically distinguishable signals associated with a fluorophore or with a combination of fluorophores.

30. A method according to claim 29, wherein the generating step includes the step of producing each digital image by imaging the hybridized chromosomal DNA with a filter having a bandpass corresponding to each of a respective one of the fluorophores.

31. A method according to claim 30, wherein the visually emphasizing step includes the steps of generating an image of the hybridized chromosomal DNA by
   a) assigning a respective color to each fluorophore; and
   b) substituting, for those portions of the digital images which represent optically distinguishable signals associated with the fluorophores, or combinations thereof, respective colors assigned thereto.

32. A method of in situ hybridization to simultaneously detect multiple target sequences of interest in chromosomal DNA from interphase cells or nuclei thereof, the method comprising:
   (a) treating a sample of interphase cells or nuclei thereof to render chromosomal DMA present therein available for hybridization to sequences complementary thereto,
   (b) contacting said sample with a pool of DNA, wherein said pool comprises:
      i) different labeled DNA probes, each DNA probe comprising either DNA fragments labeled with a single fluorophore or a mixture of DNA fragments separately labeled with different fluorophores, such that each DNA probe generates an optically distinguishable signal, and each probe being specific for one of said human chromosomes, or region thereof, suspected to be present in said sample; and ii) competitor DNA fragments, wherein said fragments comprise repetitive sequences complementary to sequences present in said sample and to sequences present in said probes, wherein the labeled DNA probes and the competitor DNA fragments are DNA fragments ranging from 150–250 nucleotides, under conditions that allow hybridization of said competitor DNA fragments to said complementary repetitive sequences present in said sample and present in said probes, sufficient to suppress cross-hybridization between said repetitive sequences in said sample and allow hybridization of said probes to specific target chromosomal sequences present in said sample; and c) detecting multiple hybridization signals simultaneously, wherein each detected signal is distinguishable and identifies a specific target chromosomal sequence present in said sample.

* * * * *

UNITED STATES PATENT AND TRADEMARK OFFICE
CERTIFICATE OF CORRECTION

PATENT NO. : 6,203,977 B1
DATED : March 20, 2001
INVENTOR(S) : David C. Ward et al.

It is certified that error appears in the above-identified patent and that said Letters Patent is hereby corrected as shown below:

Title page,
Column 1, please insert reference to the terminal disclaimer

Signed and Sealed this

Twenty-fifth Day of December, 2001

Attest:

JAMES E. ROGAN
*Attesting Officer*     *Director of the United States Patent and Trademark Office*